(12) United States Patent
Kuwahara

(10) Patent No.: US 9,901,097 B2
(45) Date of Patent: Feb. 27, 2018

(54) AGRICULTURAL AND HORTICULTURAL FUNGICIDAL COMPOSITION

(71) Applicant: Nippon Soda Co., Ltd., Chiyoda-ku, Tokyo (JP)

(72) Inventor: Raito Kuwahara, Yama-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/345,746

(22) PCT Filed: Sep. 24, 2012

(86) PCT No.: PCT/JP2012/074401
§ 371 (c)(1),
(2) Date: Mar. 19, 2014

(87) PCT Pub. No.: WO2013/047441
PCT Pub. Date: Apr. 4, 2013

(65) Prior Publication Data
US 2014/0221298 A1   Aug. 7, 2014

(30) Foreign Application Priority Data

Sep. 26, 2011   (JP) .................. 2011-209969

(51) Int. Cl.
| | | |
|---|---|---|
| *A01N 43/90* | (2006.01) | |
| *A01N 43/40* | (2006.01) | |
| *A01N 57/12* | (2006.01) | |
| *A01N 43/54* | (2006.01) | |
| *A01N 57/14* | (2006.01) | |
| *A01N 43/713* | (2006.01) | |
| *A01N 43/78* | (2006.01) | |
| *A01N 43/88* | (2006.01) | |
| *A01N 43/22* | (2006.01) | |
| *A01N 43/707* | (2006.01) | |
| *A01N 43/42* | (2006.01) | |
| *A01N 47/30* | (2006.01) | |
| *A01N 43/36* | (2006.01) | |
| *A01N 47/40* | (2006.01) | |
| *A01N 43/50* | (2006.01) | |
| *A01N 43/72* | (2006.01) | |

(52) U.S. Cl.
CPC ............ *A01N 43/90* (2013.01); *A01N 43/22* (2013.01); *A01N 43/36* (2013.01); *A01N 43/40* (2013.01); *A01N 43/42* (2013.01); *A01N 43/50* (2013.01); *A01N 43/54* (2013.01); *A01N 43/707* (2013.01); *A01N 43/713* (2013.01); *A01N 43/72* (2013.01); *A01N 43/78* (2013.01); *A01N 43/88* (2013.01); *A01N 47/30* (2013.01); *A01N 47/40* (2013.01); *A01N 57/12* (2013.01); *A01N 57/14* (2013.01)

(58) Field of Classification Search
CPC ...... A01B 12/006; A01N 43/90; A01N 43/42; A01N 43/72; A01N 43/22; A01N 43/36; A01N 43/40; A01N 43/50; A01N 43/54; A01N 43/707; A01N 43/78; A01N 43/88; A01N 47/30; A01N 47/40; A01N 57/12; A01N 57/14
See application file for complete search history.

(56) References Cited

U.S. PATENT DOCUMENTS

2011/0136782 A1   6/2011   Mitani et al.
2012/0289702 A1   11/2012  Shibayama et al.

FOREIGN PATENT DOCUMENTS

| EP | 1679003 A1 | 7/2006 |
|---|---|---|
| JP | 2002-308707 A | 10/2002 |
| JP | 2006-052195 A | 2/2006 |
| JP | 2007-112760 A | 5/2007 |

(Continued)

OTHER PUBLICATIONS

Mitani et al. WO 2010/018686, published: Feb. 18, 2010, English Translation obtained on Aug. 27, 2015.*

(Continued)

*Primary Examiner* — Johann R Richter
*Assistant Examiner* — Genevieve S Alley
(74) *Attorney, Agent, or Firm* — Foley & Lardner LLP

(57) ABSTRACT

The present invention provides an agricultural and horticultural fungicidal composition including a compound A which is at least one selected from a nitrogen-containing heterocyclic compound having a specific structure including a compound represented by the formula (1), and a salt thereof, and a compound B which is at least one selected from the group of specific pesticidally active compounds:

[Chem. 1]

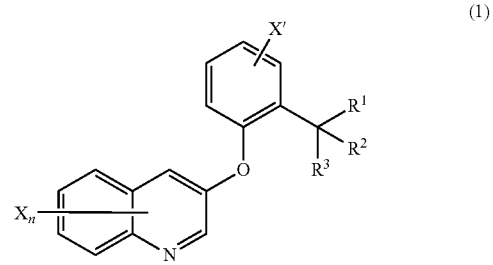

in the formula (1), X each independently represents a halogeno group or a C1 to 6 alkyl group; n represents the number of X(s) and is an integer of 0 to 6; and X' represents a halogeno group; and $R^1$, $R^2$ and $R^3$ each independently represent a C1 to 6 alkyl group or a hydroxyl group.

1 Claim, No Drawings

(56) References Cited

FOREIGN PATENT DOCUMENTS

| JP | 2010-150230 A | | 7/2010 |
|---|---|---|---|
| JP | 2010-248273 A | | 11/2010 |
| JP | 2011/012088 | * | 1/2011 |
| WO | WO 2007-014290 A2 | | 2/2007 |
| WO | WO 2010/018686 A1 | | 2/2010 |
| WO | WO 2010/139656 | * | 12/2010 |
| WO | WO 2011/081174 | * | 7/2011 |
| WO | WO 2011/081174 A1 | | 7/2011 |

OTHER PUBLICATIONS

Nomura et al., JP 2011/012088, published: Jan. 20, 2011, English Translation obtained on Aug. 28, 2015.*
Shibayama et al., WO 2011/081174, published: Jul. 7, 2011, English language translation obtained on Aug. 22, 2016.*
Hugie, J. et al., Determination of Tank-Mixture Efficacy, Syngenta Crop Protection, Des Moines, IA, Dec. 2, 2009.*
Flint, J. L. et al. Analyzing Herbicide Interactions: A Statistical Treatment of Colby's Method, Weed Technol, 1998, 2:304-309.*
International Search Report dated Nov. 20, 2012 in PCT/JP2012/074401.
Tomlin et al., The Pesticide Manual, 14$^{th}$ Edition, 2006, pp. 110, 493 and 678.
Office Action dated Jun. 8, 2017, in JP 2016-172855, with English translation.
Office Action dated Nov. 15, 2017 in KR 10-2016-7016028, with English translation.

* cited by examiner

AGRICULTURAL AND HORTICULTURAL FUNGICIDAL COMPOSITION

TECHNICAL FIELD

The present invention relates to an agricultural and horticultural fungicidal composition. More particularly, the present invention relates to an agricultural and horticultural fungicidal composition which exhibits excellent controlling effect on plant diseases even at low doses and does not pose concern for harmful effects on useful plants.

Priority is claimed on Japanese Patent Application No. 2011-209969, filed on Sep. 26, 2011, the content of which is incorporated herein by reference.

BACKGROUND ART

In the related art, a number of controlling drugs were used to control crop diseases in the cultivation of agricultural and horticultural crops. However, since the controlling effects are insufficient or the uses of the drugs are limited due to the emergence of pathogens with drug resistance, or since harmful effects or contaminations occur in plants or the toxicity to humans, animals, fish, or the like is strong, the drugs in the related art have often been insufficient to control crop diseases. Therefore, there is a demand for development of the fungicidal composition which can be safely used with a reduction in the aforementioned drawbacks. For example, it is described that a nitrogen-containing heterocyclic compound and/or a salt thereof are useful as an active ingredient in a fungicidal composition in PTLs 1 and 2.

CITATION LIST

Patent Literature

[PTL 1] Pamphlet of PCT International Publication No. WO2010/018686
[PTL 2] Pamphlet of PCT International Publication No. WO2011/081174

SUMMARY OF INVENTION

Technical Problem

An object of the present invention is to provide an agricultural and horticultural fungicidal composition which exhibits an excellent controlling effect on plant diseases even at low doses and does not pose a concern for harmful effects on useful plants.

Solution to Problem

In order to attain the object, the present inventors have made more extensive studies on fungicidal composition including the nitrogen-containing heterocyclic compound and/or a salt thereof described in PTLs 1 and 2 as an active ingredient. As a result, they have found that by using a combination of the nitrogen-containing heterocyclic compound and/or a salt thereof with a specific pesticidally active compound, an excellent controlling effect on plant diseases even at low doses are exhibited and there is no concern about harmful effects on useful plants. The present invention has been completed by further conducting repeated investigations based on the aforementioned finding.

That is, the present invention relates to the followings.

[1] An agricultural and horticultural fungicidal composition including:

at least one selected from the group consisting of a nitrogen-containing heterocyclic compound represented by the formula (1), a nitrogen-containing heterocyclic compound represented by the formula (2), and salts thereof:

[Chem. 1]

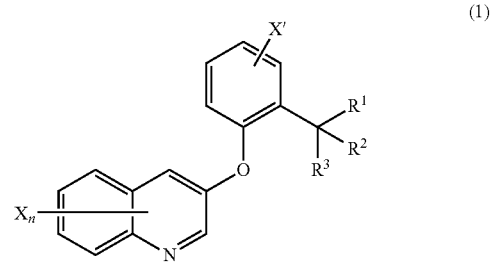

in the formula (1), X each independently represents a halogeno group or a C1 to 6 alkyl group. n represents the number of X(s) and is an integer of 0 to 6. X' represents a halogeno group. $R^1$, $R^2$ and $R^3$ each independently represent a C1 to 6 alkyl group or a hydroxyl group.

[Chem. 2]

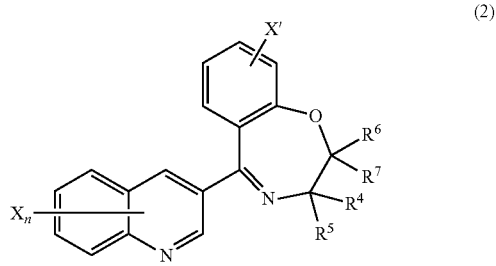

in the formula (2), X each independently represents a halogeno group or a C1 to 6 alkyl group. n represents the number of X(s) and is an integer of 0 to 6. X' represents a halogeno group. $R^4$, $R^5$, $R^6$ and $R^7$ each independently represent a hydrogen atom, a C1 to 6 alkyl group, or a hydroxyl group; and at least one compound selected from the group consisting of an SBI agent, a benzimidazole-based agent, an acid amide-based fungicide, a dicarboximide-based fungicide, a phenylpyrrole-based fungicide, an organic (thio)phosphate-based agent, a guanidine-based fungicide, a mitochondrial electron transport chain complex II inhibitor, a mitochondrial electron transport chain complex III inhibitor, an anilinopyrimidine-based agent, a neonicotinoid-based agent, an SH inhibitor, cyflufenamid, cymoxanil, proquinazid, metrafenone, quinoxyfen, diclomezine, isoprothiolane, bupirimate, hexythiazox, tebufenozide, thiodicarb, spinosad, etofenprox, fipronil, ethiprole, pymetrozine, buprofezin, chlorfenapyr, a compound represented by the formula (3), a compound represented by the formula (4), and salts thereof

[Chem. 3]

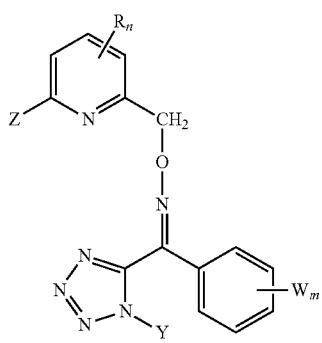

(3)

in the formula (3), W represents a C1 to 6 alkyl group, a C1 to 6 alkoxy group, a halogen atom, a nitro group, a cyano group, a C6 to 10 aryl group, or a C1 to 6 alkylsulfonyl group. Y represents a C1 to 6 alkyl group. m represents the number of W(s) and is an integer of 0 to 5. Z represents a hydrogen atom, an amino group, or a group represented by the formula: —NHC(=O)-Q, in which Q represents a hydrogen atom, a C1 to 8 alkyl group, a C1 to 6 haloalkyl group, a C3 to 6 cycloalkyl group, a C1 to 8 alkoxy group, a C3 to 6 cycloalkyloxy group, a C7 to 20 aralkyloxy group, a C1 to 4 alkylthio-C1 to 8 alkyl group, a C1 to 4 alkoxy-C1 to 2 alkyl group, a C1 to 4 acylamino-C1 to 6 alkyl group, a C1 to 4 acylamino-C1 to 6 alkoxy group, a C1 to 8 alkylamino group, a C2 to 6 alkenyl group, an aralkyl group, or a phenyl group. R represents a halogen atom. n represents the number of R(s) and is an integer of 0 to 3.

[Chem. 4]

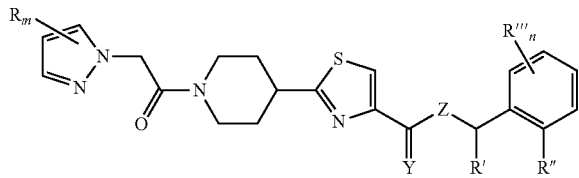

(4)

in the formula (4), Y represents a group represented by O or NR$^1$, in which R$^1$ represents a hydrogen atom or a methyl group. Z represents a group represented by CR$^2$R$^3$ or NR$^2$, in which R$^2$ and R$^3$ independently represent a hydrogen atom or a methyl group. R represents a hydroxyl group, a halogen atom, a C1 to 4 alkyl group, a C1 to 4 haloalkyl group, a C1 to 4 alkoxy group, or a C1 to 4 haloalkoxy group. m represents the number of R(s) and is an integer of 0 to 3. R' and R" independently represent a hydrogen atom, a hydroxyl group, a halogen atom, a C1 to 4 alkyl group, a C1 to 4 haloalkyl group, a C1 to 4 alkoxy group, or a C1 to 4 haloalkoxy group. R'" represents a hydroxyl group, a halogen atom, a C1 to 4 alkyl group, a C1 to 4 haloalkyl group, a C1 to 4 alkoxy group, or a C1 to 4 haloalkoxy group. n represents the number of R'" and is an integer of 0 to 4. And, =Y and R' may be combined to represent a group represented by =N—O—, and R' and R" may be combined to represent a C2 to 3 alkylene group.

[2] The agricultural and horticultural fungicidal composition as described in [1], in which the SBI agent is at least one selected from the group consisting of triflumizole, difenoconazole, and tebuconazole.

[3] The agricultural and horticultural fungicidal composition as described in [1] or [2], in which the benzimidazole-based agent is thiophanate-methyl.

[4] The agricultural and horticultural fungicidal composition as described in any one of [1] to [3], in which the acid amide-based fungicide is at least one selected from the group consisting of metalaxyl, benthiavalicarb-isopropyl, fluopicolide, fluopyram, zoxamide, flutolanil, carboxin, thifluzamide, and boscalid.

[5] The agricultural and horticultural fungicidal composition as described in any one of [1] to [4], in which the dicarboxylmide-based fungicide is iprodione.

[6] The agricultural and horticultural fungicidal composition as described in any one of [1] to [5], in which the phenylpyrrole-based fungicide is fludioxonil.

[7] The agricultural and horticultural fungicidal composition as described in any one of [1] to [6], in which the organic (thio)phosphate-based agent is at least one selected from the group consisting of compounds represented by the formula (5):

[Chem. 5]

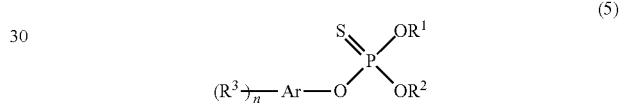

(5)

in the formula (5), R' and R$^2$ represent a methyl group or an ethyl group. Ar represents a phenyl group or a 6-membered heteroaromatic ring group. R$^3$ represents a halogen atom or a methyl group. n represents the number of R$^3$ and is an integer of 0 to 5.

[8] The agricultural and horticultural fungicidal composition as described in any one of [1] to [7], in which the organic (thio)phosphate-based agent is at least one selected from the group consisting of fosetyl, tolclofos-methyl, and chlorpyrifos.

[9] The agricultural and horticultural fungicidal composition as described in any one of [1] to [8], in which the guanidine-based fungicide is iminoctadine.

[10] The agricultural and horticultural fungicidal composition as described in any one of [1] to [9], in which the mitochondrial electron transport chain complex II inhibitor is at least one including an anilide-based fungicide.

[11] The agricultural and horticultural fungicidal composition as described in any one of [1] to [10], in which the mitochondrial electron transport chain complex III inhibitor is at least one selected from the group consisting of a QoI agent, a QiI agent, and ametoctradin.

[12] The agricultural and horticultural fungicidal composition as described in [11], in which the QoI agent is at least one selected from the group consisting of trifloxystrobin, azoxystrobin, kresoxim-methyl, orysastrobin, famoxadone, and pyribencarb.

[13] The agricultural and horticultural fungicidal composition as described in [11] or [12], in which the QiI agent is cyazofamid.

[14] The agricultural and horticultural fungicidal composition as described in any one of [1] to [13], in which the anilinopyrimidine-based agent is cyprodinil.

[15] The agricultural and horticultural fungicidal composition as described in any one of [1] to [14], in which the neonicotinoid-based agent is at least one selected from the group consisting of compounds represented by the formula (6):

[Chem. 6]

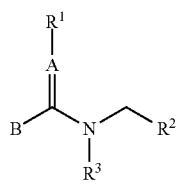

(6)

in the formula (6), A represents N or CH. B represents a methyl group or a group represented by —NR$^{21}$R$^{22}$, wherein R$^{21}$ represents a hydrogen atom or a methyl group, and R$^{22}$ represents a methyl group or is combined with R$^3$ to form a 5- to 6-membered ring. R$^1$ represents a cyano group or a nitro group. R$^2$ represents an unsubstituted or substituted 5- to 6-membered heterocyclic group. R$^3$ represents a hydrogen atom, a methyl group, or an ethyl group or is combined with R$^{22}$ to form a 5- to 6-membered ring.

[16] The agricultural and horticultural fungicidal composition as described in any one of [1] to [15], in which the neonicotinoid-based agent is at least one selected from the group consisting of acetamiprid, imidacloprid, thiamethoxam, clothianidin, and dinotefuran.

[17] The agricultural and horticultural fungicidal composition as described in any one of [1] to [16], in which the SH inhibitor is at least one selected from the group consisting of manzeb, thiram, chlorothalonil, captan, folpet, and fluazinam.

[18] The agricultural and horticultural fungicidal composition as described in any one of [1] to [17], in which the compound represented by the formula (3) is a compound represented by the formula (7):

[Chem. 7]

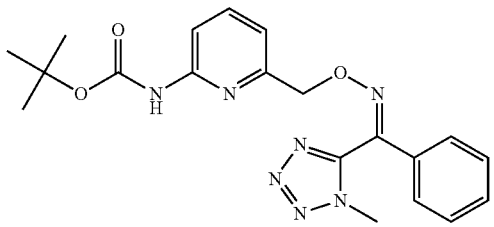

(7)

[19] The agricultural and horticultural fungicidal composition as described in any one of [1] to [18], in which the compound represented by the formula (4) is a compound represented by the formula (8) or the formula (9):

[Chem. 8]

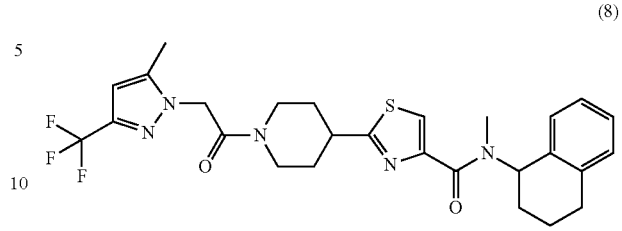

(8)

[Chem. 9]

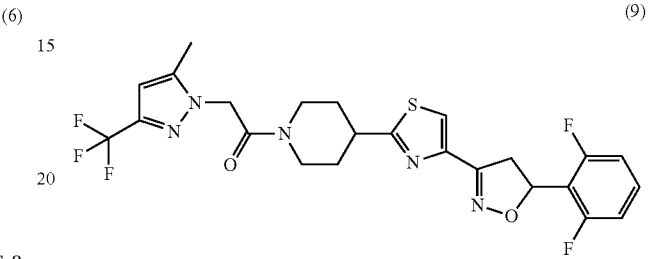

(9)

Advantageous Effects of Invention

The agricultural and horticultural fungicidal composition of the present invention exhibits an excellent controlling effect on plant diseases even at very low doses and does not pose a concern about harmful effects on useful plants.

DESCRIPTION OF EMBODIMENTS

The agricultural and horticultural fungicidal composition of the present invention includes at least one selected from the group consisting of a nitrogen-containing heterocyclic compound having a specific structure and a salt thereof (which may be hereinafter sometimes referred to a compound A), and at least one selected from the group of specific pesticidally active compounds (which may be hereinafter sometimes referred to a compound B). The agricultural and horticultural fungicidal composition of the present invention exhibits a remarkably synergistic controlling effect on plant diseases, which could not be predicted from controlling effect on plant diseases obtained from the use of the compound A alone or the compound B alone.

(Compound A)

The compound A is at least one selected from the group consisting of the nitrogen-containing heterocyclic compound represented by the formula (1), the nitrogen-containing heterocyclic compound represented by the formula (2), and salts thereof.

X in the formula (1) or the formula (2) each independently represents a halogeno group or a C1 to 6 alkyl group. n represents the number of X(s) and is an integer of 0 to 6.

Examples of the C1 to 6 alkyl group in X include a methyl group, an ethyl group, an n-propyl group, an i-propyl group, an n-butyl group, an s-butyl group, an i-butyl group, a t-butyl group, an n-pentyl group, and an n-hexyl group. In the C1 to 6 alkyl group, a part or all of the hydrogen atoms may be substituted with other group(s) within a range not interfering with the effect of the present invention. Examples of the substituent include a halogeno group and a hydroxyl group.

Examples of the halogeno group in X include a fluoro group, a chloro group, a bromo group, and an iodo group.

X' in the formula (1) or the formula (2) represents a halogeno group. The halogeno group in X' has the same meaning as in X.

$R^1$, $R^2$ and $R^3$ in the formula (1) each independently represent a C1 to 6 alkyl group or a hydroxyl group. The C1 to 6 alkyl group in R' $R^2$ and $R^3$ have the same meanings as in X.

$R^4$, $R^5$, $R^6$ and $R^7$ in the formula (2) each independently represent a hydrogen atom, a C1 to 6 alkyl group, or a hydroxyl group. The C1 to 6 alkyl group in $R^4$, $R^5$, $R^6$ and $R^7$ have the same meanings as in X.

The salt of the nitrogen-containing heterocyclic compound represented by the formula (1) or the formula (2) is not particularly limited as long as it is agriculturally and horticulturally acceptable salt, and examples thereof include salts of inorganic acids, such as hydrochloride, nitrate, sulfate, and phosphate; and salts of organic acids, such as acetate, lactate, propionate, and benzoate.

The nitrogen-containing heterocyclic compound represented by the formula (1) used in the present invention is a known material and specific examples thereof include the compounds described in the pamphlet of PCT International Publication No. WO2011/081174. Further, the nitrogen-containing heterocyclic compound represented by the formula (1) and a salt thereof can be prepared by a known method. Specific examples of the preparation method therefor include the methods described in the pamphlet of PCT International Publication No. WO2011/081174.

The nitrogen-containing heterocyclic compound represented by the formula (2) used in the present invention is a known material and specific examples thereof include the compounds described in the pamphlet of PCT International Publication No. WO2010/018686. Further, the nitrogen-containing heterocyclic compound represented by the formula (2) and a salt thereof can be prepared by a known method. Specific examples of the preparation method therefor include the methods described in the pamphlet of PCT International Publication No. WO2010/018686.

(Compound B)

The compound B is at least one compound selected from the group consisting of:

an SBI agent, a benzimidazole-based agent, an acid amide-based fungicide, a dicarboximide-based fungicide, a phenylpyrrole-based fungicide, an organic (thio)phosphate-based agent, a guanidine-based fungicide, a mitochondrial electron transport chain complex II inhibitor, a mitochondrial electron transport chain complex III inhibitor, an anilinopyrimidine-based agent, a neonicotinoid-based agent, an SH inhibitor, cyflufenamid, cymoxanil, proquinazid, metrafenone, quinoxyfen, diclomezine, isoprothiolane, bupirimate, hexythiazox, tebufenozide, thiodicarb, spinosad, etofenprox, fipronil, ethiprole, pymetrozine, buprofezin, chlorfenapyr, a compound represented by the formula (10), a compound represented by the formula (11), and salts thereof:

[Chem. 10]

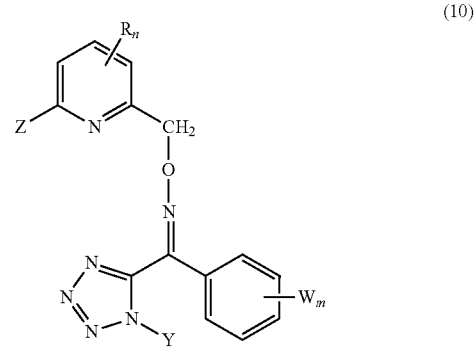

(10)

in the formula (10), W represents a C1 to 6 alkyl group, a C1 to 6 alkoxy group, a halogen atom, a nitro group, a cyano group, a C6 to 10 aryl group, or a C1 to 6 alkylsulfonyl group. Y represents a C1 to 6 alkyl group. m represents the number of W(s) and is an integer of 0 to 5. Z represents a hydrogen atom, an amino group, or a group represented by the formula: —NHC(═O)-Q, in which Q represents a hydrogen atom, a C1 to 8 alkyl group, a C1 to 6 haloalkyl group, a C3 to 6 cycloalkyl group, a C1 to 8 alkoxy group, a C3 to 6 cycloalkyloxy group, a C7 to 20 aralkyloxy group, a C1 to 4 alkylthio-C1 to 8 alkyl group, a C1 to 4 alkoxy-C1 to 2 alkyl group, a C1 to 4 acylamino-C1 to 6 alkyl group, a C1 to 4 acylamino-C1 to 6 alkoxy group, a C1 to 8 alkylamino group, a C2 to 6 alkenyl group, an aralkyl group, or a phenyl group. R represents a halogen atom. n represents the number of R(s) and is an integer of 0 to 3.

[Chem. 11]

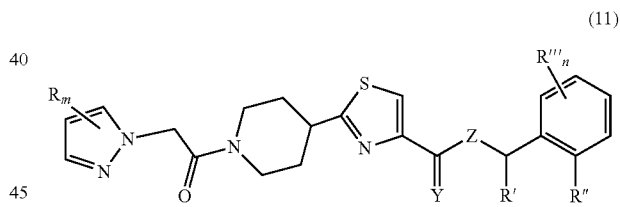

(11)

in the formula (11), Y represents a group represented by O or $NR^1$, in which $R^1$ represents a hydrogen atom or a methyl group. Z represents a group represented by $CR^2R^3$ or $NR^2$, in which $R^2$ and $R^3$ independently represent a hydrogen atom or a methyl group. R represents a hydroxyl group, a halogen atom, a C1 to 4 alkyl group, a C1 to 4 haloalkyl group, a C1 to 4 alkoxy group, or a C1 to 4 haloalkoxy group. m represents the number of R(s) and is an integer of 0 to 3. R' and R" independently represent a hydrogen atom, a hydroxyl group, a halogen atom, a C1 to 4 alkyl group, a C1 to 4 haloalkyl group, a C1 to 4 alkoxy group, or a C1 to 4 haloalkoxy group. R'" represents a hydroxyl group, a halogen atom, a C1 to 4 alkyl group, a C1 to 4 haloalkyl group, a C1 to 4 alkoxy group, or a C1 to 4 haloalkoxy group. n represents the number of R'" and is an integer of 0 to 4. And, ═Y and R' may be combined with each other to represent a group represented by ═N—O—, and R' and R" may be combined to represent a C2 to 3 alkylene group.

The compound represented by the formula (11) is preferably a compound represented by the formula (12).

[Chem. 12]

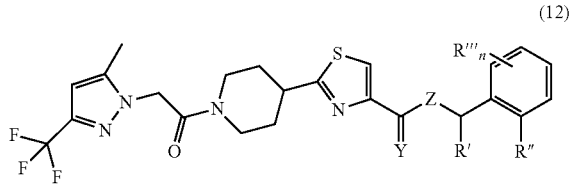

(12)

in the formula (12), Y, Z, R', R", R''', and n have the same meanings as Y, Z, R', R", R''', and n described in the formula (11).

Additionally, the compound B further includes an optically active compound thereof. For example, it is in the same case as metalaxyl M with respect to metalaxyl. The compound B includes known materials and these may be available according to known preparation methods or by purchasing from manufacturers.

The SBI agent (sterol biosynthesis inhibitor) as mentioned in the present invention refers to a group of the compounds that inhibit ergosterol biosynthesis. Preferred examples of the SBI agent include triflumizole, difenoconazole, tebuconazole, bromuconazole, cyproconazole, fenbuconazole, flusilazole, flutriafol, hexaconazole, propiconazole, tetraconazole, triadimefon, triadimenol, triflumizole, bitertanol, imibenconazole, diniconazole, diniconazole M, epoxiconazole, fluquinconazole, prochloraz, metconazole, ipconazole, myclobutanil, penconazole, fenarimol, pefurazoate, pyrifenox, triforine, diclobutrazol, fluotrimazol, imazalil, imazalil-sulfate, simeconazole, triticonazole, etaconazole, nuarimol, azaconazole, fluconazole, oxpoconazole, buthiobate, prothioconazole, naftifine, uniconazole P, viniconazole, voriconazole, fenpropimorph, fenpropidin, tridemorph, dodemorph, aldimorph, fenpropidin, piperalin, spiroxamine, fenhexamid, pyributicarb, and terbinafine.

As a representative group of the compounds included in the SBI agent, there is a DMI agent (demethylase inhibitor) that binds to a 14α demethylase (CYP51), which is one kind of Cytochrome P450 to inhibit demethylation of sterol C14 or so. Preferred examples of the DMI agent include triflumizole, difenoconazole, tebuconazole, bromuconazole, cyproconazole, fenbuconazole, flusilazole, flutriafol, hexaconazole, propiconazole, tetraconazole, triadimefon, triadimenol, triflumizole, bitertanol, imibenconazole, diniconazole, diniconazole M, epoxyconazole, fluquinconazole, prochloraz, metconazole, ipconazole, myclobutanil, penconazole, fenarimol, pefurazoate, pyrifenox, triforine, diclobutrazol, fluotrimazol, imazalil, imazalil.sulfate, simeconazole, triticonazole, etaconazole, nuarimol, azaconazole, fluconazole, oxpoconazole, buthiobate, prothioconazole, naftifine, uniconazole P, viniconazole, and voriconazole.

Among these, particularly preferred examples of the compound include triflumizole, difenoconazole, and tebuconazole.

The benzimidazole-based agent as mentioned in the present invention refers to a group of the compounds having a benzimidazole skeleton and binding to a tubulin constituting microtubules to inhibit nuclear division, and a precursor thereof, and a group of the compounds that are transformed to forms having benzimidazole skeletons to exert the same inhibitory effect. Preferred examples of the benzimidazole-based agent include benomyl, carbendazim, fuberidazole, chlorfenazole, and thiabendazole, and examples of the precursor include thiophanate and thiophanate-methyl.

Among these, particularly preferred examples of the compound include thiophanate-methyl.

The acid amide-based fungicide as mentioned in the present invention is a group of the compounds having a fungicidal effect, which has a carboxyl acid amide structure. Preferred examples of the acid amide-based fungicide include fluopyram, flutolanil, carboxin, oxycarboxin, thifluzamide, boscalid, penthiopyrad, mepronil, furametpyr, isofetamid, penflufen, metalaxyl, benthiavalicarb-isopropyl, fluopicolide, zoxamide, pencycuron, tiadinil, zarilamid, dimethomorph, flumorph, iprovalicarb, mandipropamid, and valifenalate.

As a representative group of the compounds included in the acid amide-based fungicides, there is a group of the compounds which are called anilide-based fungicides. These generally have structures of the formula (13).

[Chem. 13]

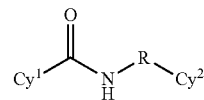

(13)

in the formula (13), $Cy^1$ and $Cy^2$ independently represent an unsubstituted or substituted phenyl group, or an unsubstituted or substituted 5- to 6-membered heterocyclic group, and R represents a single bond, a methylene group, or an ethylene group.

Furthermore, the mitochondrial electron transport chain complex II inhibitor as mentioned in the present invention is a group of the compounds having a property of binding to a mitochondrial electron transport chain complex II (succinic acid dehydrogenase complex) to inhibit respiration.

Representative Examples of the group of the compounds included in the mitochondrial electron transport chain complex II inhibitor include the anilide fungicides as described above.

Preferred examples of the anilide fungicide include fluopyram, flutolanil, carboxin, oxycarboxin, thifluzamide, boscalid, penthiopyrad, mepronil, furametpyr, isofetamid, penflufen, benodanil, fenfuram, bixafen, isopyrazam, fluxapyroxad, and sedaxane.

Particularly preferred examples of the compound out of the group of the compounds listed as the acid amide-based fungicide or the mitochondrial electron transport chain complex II inhibitor include fluopyram, flutolanil, carboxin, thifluzamide, boscalid, metalaxyl, benthiavalicarb-isopropyl, fluopicolide, and zoxamide.

The dicarboxylmide-based fungicide as mentioned in the present invention is a group of the compounds having 5-membered rings including dicarboxylmide structures, and targets a signal transduction system protein OS-1 with respect to the osmotic pressure control in fungi. Preferred examples of the dicarboxylmide-based fungicide include iprodione, procymidone, vinclozolin, chlozolinate, and fluoroimide.

Among these, particularly preferred examples of the compound include iprodione.

The phenylpyrrole-based fungicide as mentioned in the present invention is a group of the compounds having 3-phenylpyrrole structures, and targets a signal transduction system protein OS-2 with respect to the osmotic pressure control in fungi. Preferred examples of the phenylpyrrole-based fungicide include fludioxonil and fenpiclonil.

Among these, particularly preferred examples of the compound include fludioxonil.

The organic (thio)phosphate-based agent as mentioned in the present invention is a group of the compounds having phosphate ester structures or thiophosphate ester structures, and examples thereof include organic (thio)phosphate-based fungicides and organic (thio)phosphate-based insecticides. Examples of the organic (thio)phosphate-based fungicides include EDDP, IBP, tolclofos-methyl, fosetyl and pyrazophos. Examples of the organic (thio)phosphate-based insecticide include DDVP, cadusafos, marathon, dimethoate, vamidothion, phosalone, pyraclofos, azinphos-methyl, azinphos-ethyl, pyrazophos, flupyrazophos, chlorpyrifos, chlorpyrifos-methyl, chlorpyrifos-ethyl, diazinon, methidathion, chlorthiophos, fenitrothion, fenthion, parathion, parathion methyl, acephate, azamethiphos, bromophos-ethyl, bromfenvinphos, BRP, chlorfenvinphos, carbophenothion, chloroethoxyphos, chloromephos, coumaphos, cyanofenphos, cyanophos, CYAP, dichlorvos, dicrotophos, disulfoton, demeton-5-methyl, dimethylvinphos, demeton-5-methylsulfone, dialiphos, diazinon, diclofenthion, dioxabenzophos, disulfoton, ethion, ethoprophos, etrimfos, EPN, fenamiphos, fensulfothion, fonofos, formothion, phosmethylan, heptenophos, isazophos, iodinefenphos, isofenphos, isoxathion, iprobenfos, malathion, mevinphos, methamidophos, monocrotophos, mecarbam, metacriphos, naled, omethoate, oxydemeton-methyl, paraoxon, phenthoate, phosmet, phosphamidon, phorate, phoxim, pirimiphos-methyl, pirimiphos-ethyl, profenofos, prothiofos, fosthiazate, phosphocarb, propaphos, propetamphos, prothoate, pyridaphenthion, quinalphos, salithion, sulprophos, sulfotep, tetrachlorvinphos, terbufos, triazophos, trichlorfon, tebupirimfos, temephos, and thiometon.

Among these, a preferred compound is a compound represented by the formula (14).

[Chem. 14]

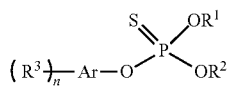

(14)

in the formula (14), $R^1$ and $R^2$ represent a methyl group or an ethyl group. Ar represents a phenyl group or a 6-membered heteroaromatic ring group. $R^3$ represents a halogen atom or a methyl group. n represents the number of $R^3$ and is an integer of 0 to 5.

Among the organic (thio)phosphate-based agents, more preferred examples of the compound include fosetyl, tolclofos-methyl, and chlorpyrifos.

The guanidine-based fungicide as mentioned in the present invention refers to a group of the compounds having guanidine partial structures. Preferred examples of the guanidine-based fungicide include iminoctadine acetate, iminoctadine albesilate, dodine, and guazatine.

The mitochondrial electron transport chain complex III inhibitor as mentioned in the present invention refers to a group of compound having a property of binding to a mitochondrial electron transport chain complex III (bcl complex) to inhibit the respiration, and is used in the applications of fungicides, acaricides, or the like. These can be divided into Qo site inhibitors (QoI agents), Qi site inhibitors (QiI agents), and other compounds according to the binding sites in the complex III.

Representative examples of the group of the compounds that are QoI agents include strobilurin-based agents, as well as famoxadone and pyribencarb. Examples of the QiI agent include cyazofamid, amisulbrom, fenamidone, and furmecyclox, and cyazofamid is particularly preferred. Other examples of the compound include ametoctradin and tebufloquin, and ametoctradin is particularly preferable.

The strobilurin-based agent refers to a group of the compounds having partial structures of a 3-methoxyacrylic ester (methoxyacrylate-based), an N-methoxycarbamic ester (methoxycarbamate-based), an methoxyiminoacetic ester (methoxyiminoacetate-based), a 2-methoxyiminoacetamide (methoxyiminoacetamide-based), or the like, and binding to a Qo site of a respiration chain complex III to inhibit the respiration. Examples of the strobilurin-based agent include methoxyacrylate-based azoxystrobin, picoxystrobin, pyraoxystrobin, enestroburin, and phenoxystrobin; methoxycarbamate-based pyraclostrobin, pyrametostrobin, and triclopyricarb; methoxyiminoacetate-based kresoxim-methyl, and trifloxystrobin; methoxyiminoacetamide-based orysastrobin, metominostrobin, metominofen, and dimoxystrobin; as well as fluoxastrobin.

A preferred compound as the strobilurin-based agent is a compound represented by the formula (15).

[Chem. 15]

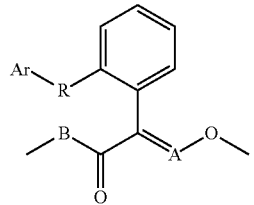

(15)

in the formula (15), A represents a CH or N. B represents O or NH. Ar—R— represents a group represented by any one of Ar—O—, Ar—CH$_2$—, Ar—CH$_2$O—, Ar—OCH$_2$—, and Ar—C(CH$_3$)=NOCH$_2$—, and Ar represents an unsubstituted or substituted phenyl group or an unsubstituted or substituted 6-membered heteroaromatic ring group.

Among the strobilurin-based agents, more preferred examples of the compound include trifloxystrobin, kresoxim-methyl, azoxystrobin, and orysastrobin.

The anilinopyrimidine-based agent as mentioned in the present invention is a fungicide which has a 2-phenylaminopyrimidine skeleton and has an action of inhibiting methionine biosynthesis and an action of inhibiting the secretion of cell wall degrading enzymes. Preferred examples of the anilinopyrimidine-based agent include andoprim, cyprodinil, mepanipyrim, and pyrimethanil. Among these, cyprodinil is particularly preferable.

The neonicotinoid-based agent as mentioned in the present invention is an insecticide which functions as a blocking agent for a nicotinic acetylcholine receptor. Examples of the neonicotinoid-based agent include acetamiprid, imidacloprid, thiamethoxam, clothianidin, dinotefuran, nitenpyram, and thiacloprid. A preferred compound as the neonicotinoid-based agent is a compound represented by the formula (16).

[Chem. 16]

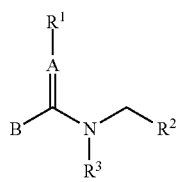

(16)

[Chem. 19]

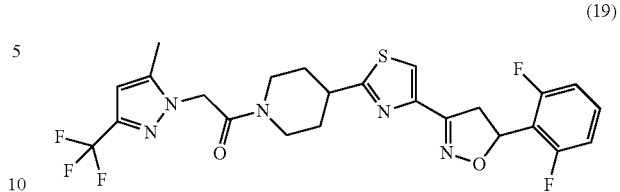

(19)

in the formula (16), A represents N or CH. B represents a methyl group or a group represented by —NR$^{21}$R$^{22}$, wherein R$^{21}$ represents a hydrogen atom or a methyl group, and R$^{22}$ represents a methyl group or is combined with R$^3$ to form a 5- to 6-membered ring. R$^1$ represents a cyano group or a nitro group. R$^2$ represents an unsubstituted or substituted 5- to 6-membered heterocyclic group. R$^3$ represents a hydrogen atom, a methyl group, or an ethyl group or is combined with R$^{22}$ to form a 5- to 6-membered ring.

Among these, particularly preferred examples of the compound include acetamiprid, imidacloprid, thiamethoxam, clothianidin, and dinotefuran.

The SH inhibitor as mentioned in the present invention refers to a protective fungicide that inhibits mainly enzymes in the respiratory system, having an SH group, and has a spore germination inhibitory activity, and thus, has no therapeutic activity. Preferred examples of the SH inhibitor include inorganic copper, organic copper, zineb, maneb, manzeb, ziram, polycarbamate, thiram, chlorothalonil, fluazinam, captan, captafol, folpet, methyl bromide, dazomet, pyridinitrile, anilazine, dichlofluanid, dichlone, fluoroimide, and dithianon.

Among these, particularly preferred examples of the compound include manzeb, thiram, chlorothalonil, fluazinam, captan, and folpet.

The compound represented by the formula (10) is not particularly limited, but is particularly preferably a compound represented by the formula (17).

[Chem. 17]

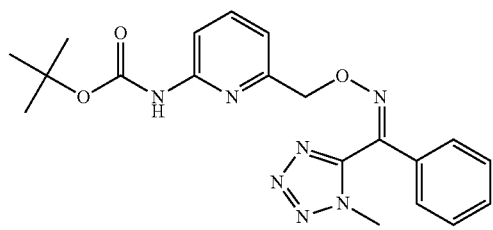

(17)

The compound represented by the formula (12) is not particularly limited, but is particularly preferably a compound represented by the formula (18) or the formula (19).

[Chem. 18]

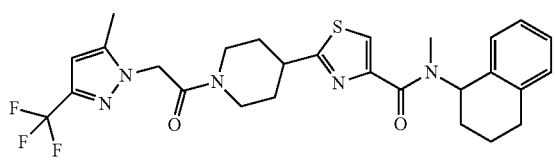

(18)

Additionally, the meanings of "unsubstituted" and "substituted" in the description above are as follows.

The term "unsubstituted" means that there is only a group which is a scaffold. A description in which there is no description of "substituted" with only the names of the groups which are scaffolds has the same meaning as "unsubstituted" unless otherwise mentioned.

On the other hand, the term "substituted" means that any hydrogen atom of the groups which are scaffolds is substituted with a group having a structure of the same as or different from the scaffold. Accordingly, the "substituent" is another group binding to a group which is a scaffold. The number of the substituent(s) may be one, or two or more. The two or more substituents may be the same as or different from each other.

The term "C1-6" or the like denotes that the number of carbon atoms of a group to be a scaffold is 1 to 6, or the like. For the number of carbon atoms, the number of the carbon atoms in the substituent is not counted. For example, the butyl group having an ethoxy group as a substituent is classified as a C2 alkoxy-C4 alkyl group.

The "substituent" is chemically allowed and is not particularly limited as long as it has the effect of the present invention.

Examples of the group that can be a "substituent" include halogeno groups such as a fluoro group, a chloro group, a bromo group, and an iodo group; C1-6 alkyl groups such as a methyl group, an ethyl group, an n-propyl group, an i-propyl group, an n-butyl group, an s-butyl group, an i-butyl group, a t-butyl group, an n-pentyl group, and an n-hexyl group; C3-6 cycloalkyl groups such as a cyclopropyl group, a cyclobutyl group, a cyclopentyl group, and a cyclohexyl group; C2-6 alkenyl groups such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; C3-6 cycloalkenyl groups such as a 2-cyclopropenyl group, a 2-cyclopentenyl group, and a 3-cyclohexenyl group; C2-6 alkynyl groups such as an ethynyl group, an 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group;

C1-6 alkoxy groups such as a methoxy group, an ethoxy group, an n-propoxy group, an i-propoxy group, an n-butoxy group, an s-butoxy group, an i-butoxy group, and a t-butoxy group; C2-6 alkenyloxy groups such as a vinyloxy group, an allyloxy group, a propenyloxy group, and a butenyloxy group; C2-6 alkynyloxy groups such as an ethynyloxy group and a propargyloxy group; C6-10 aryl groups such as a phenyl group and a naphthyl group; C6-10 aryloxy groups such as a phenoxy group and a 1-naphthoxy group; C7-11 aralkyl groups such as a benzyl group and a phenethyl group; C7-11 aralkyloxy groups such as a benzyloxy group and a phenethyloxy group; C1-7 acyl groups such as a formyl group, an acetyl group, a propionyl group, a benzoyl group, and a cyclohexylcarbonyl group; C1-7 acyloxy groups such as a formyloxy group, an acetyloxy group, a propionyloxy group, a benzoyloxy group, and a cyclohexylcarbonyloxy group; C1-6 alkoxycarbonyl groups such as a methoxycarbonyl group, an ethoxycarbonyl group, an n-propoxycarbonyl group, an i-propoxycarbonyl group, an n-butoxycarbonyl group, and a t-butoxycarbonyl group; a carboxyl group;

a hydroxyl group; an oxo group; C1-6 haloalkyl groups such as a chloromethyl group, a chloroethyl group, a trifluoromethyl group, a 1,2-dichloro-n-propyl group, a 1-fluoro-n-butyl group, and a perfluoro-n-pentyl group; C2-6 haloalkenyl groups such as a 2-chloro-1-propenyl group and a 2-fluoro-1-butenyl group; C2-6 haloalkynyl groups such as a 4,4-dichloro-1-butynyl group, a 4-fluoro-1-pentynyl group, and a 5-bromo-2-pentynyl group; C1-6 haloalkoxy groups such as a 2-chloro-n-propoxy group and a 2,3-dichlorobutoxy group; C2-6 haloalkenyloxy groups such as a 2-chloropropenyloxy group and a 3-bromobutenyloxy group; C6-10 haloaryl groups such as a 4-chlorophenyl group, a 4-fluorophenyl group, and a 2,4-dichlorophenyl group; C6-10 haloaryloxy groups such as a 4-fluorophenyloxy group and a 4-chloro-1-naphthoxy group; C1-7 haloacyl groups such as a chloroacetyl group, a trifluoroacetyl group, a trichloroacetyl group, and a 4-chlorobenzoyl group;

a cyano group; an isocyano group; a nitro group; an isocyanato group; a cyanato group; an azide group; an amino group; C1-6 alkylamino groups such as a methylamino group, a dimethylamino group, and a diethylamino group; C6-10 arylamino groups such as an anilino group and a naphthylamino group; C7-11 aralkylamino groups such as a benzylamino group and a phenylethylamino group; C1-7 acylamino groups such as a formylamino group, an acetylamino group, a propanoylamino group, a butyrylamino group, an i-propylcarbonylamino group, and a benzoylamino group; C1-6 alkoxycarbonylamino groups such as a methoxycarbonylamino group, an ethoxycarbonylamino group, an n-propoxycarbonylamino group, and an i-propoxycarbonylamino group; a carbamoyl group; substituted carbamoyl groups such as a dimethylcarbamoyl group, a phenylcarbamoyl group, and an N-phenyl-N-methylcarbamoyl group; imino-C1-6 alkyl groups such as an iminomethyl group, a (1-imino)ethyl group, and a (1-imino)-n-propyl group; hydroxyimino-C1-6 alkyl groups such as a hydroxyiminomethyl group, a (1-hydroxyimino)ethyl group, and a (1-hydroxyimino)propyl group; C1-6 alkoxyimino-C1-6 alkyl groups such as a methoxyiminomethyl group and a (1-methoxyimino)ethyl group;

a mercapto group; an isothiocyanato group; a thiocyanato group; C1-6 alkylthio groups such as a methylthio group, an ethylthio group, an n-propylthio group, an i-propylthio group, an n-butylthio group, an i-butylthio group, an s-butylthio group, and a t-butylthio group; C2-6 alkenylthio groups such as a vinylthio group and an allylthio group; C2-6 alkynylthio groups such as an ethynylthio group and a propargylthio group; C6-10 arylthio groups such as a phenylthio group and a naphthylthio group; heteroarylthio groups such as a thiazolylthio group and a pyridylthio group; C7-11 aralkylthio groups such as a benzylthio group and a phenethylthio group; (C1-6 alkylthio)carbonyl groups such as a (methylthio)carbonyl group, an (ethylthio)carbonyl group, an (n-propylthio)carbonyl group, an (i-propylthio) carbonyl group, an (n-butylthio)carbonyl group, an (i-butylthio)carbonyl group, an (s-butylthio)carbonyl group, and a (t-butylthio)carbonyl group;

C1-6 alkylsulfinyl groups such as a methylsulfinyl group, an ethylsulfinyl group, and a t-butylsulfinyl group; C2-6 alkenylsulfinyl groups such as an allylsulfinyl group; C2-6 alkynylsulfinyl groups such as a propargylsulfinyl group; C6-10 arylsulfinyl groups such as a phenylsulfinyl group; heteroarylsulfinyl groups such as a thiazolylsulfinyl group and a pyridylsulfinyl group; C7-11 aralkylsulfinyl groups such as a benzylsulfinyl group and a phenethylsulfinyl group; C1-6 alkylsulfonyl groups such as a methylsulfonyl group, an ethylsulfonyl group, and a t-butylsulfonyl group; C2-6 alkenylsulfonyl groups such as an allylsulfonyl group; C2-6 alkynylsulfonyl groups such as a propargylsulfonyl group; C6-10 arylsulfonyl groups such as a phenylsulfonyl group; heteroarylsulfonyl groups such as a thiazolylsulfonyl group and a pyridylsulfonyl group; C7-11 aralkylsulfonyl groups such as a benzylsulfonyl group and a phenethylsulfonyl group;

5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; 6-membered heteroaryl groups such as a pyridyl group, a pyrazinyl group, a pyrimidinyl group, a pyridazinyl group, and a triazinyl group; saturated heterocyclic groups such as a an aziridinyl group, an epoxy group, a pyrrolidinyl group, a tetrahydrofuranyl group, a piperidyl group, a piperazinyl group, and a morpholinyl group; tri-C1-6 alkylsilyl groups such as a trimethylsilyl group, a triethylsilyl group, and a t-butyldimethylsilyl group; and a triphenylsilyl group.

Furthermore, these "substituents" may have other "substituent(s)" therein. For example, a butyl group as a substituent may have an ethoxy group as another substituent, that is, an ethoxybutyl group.

In the agricultural and horticultural fungicidal composition of the present invention, the weight ratio of the compound A to the compound B, (compound A):(compound B), is usually 1:10,000,000 to 10,000,000:1, is preferably 1:1,000,000 to 1,000,000:1, is more preferably 1:100,000 to 100,000:1, and is particularly preferably 1:10,000 to 10,000:1.

For the agricultural and horticultural fungicidal composition of the present invention, known insecticide, acaricides, herbicides, plant growth regulators, or the like may be used in mixture, in addition to the compound A and the compound B, leading to a labor-saving effect in some cases.

Examples of the method for preparing the fungicidal composition of the present invention include (a) a method including formulating a compound A and a compound B as separate preparations, and mixing the preparations together, (b) a method including formulating a compound A as a preparation and mixing the preparation with a compound B, (c) a method including formulating a compound B as a preparation and mixing the preparation with a compound A, and (d) a method including mixing a compound A and a compound B, and if desired, formulating the mixture as a preparation.

The fungicidal composition of the present invention may include a fertilizer, a solid carrier, a thickener, a surfactant, a spreading agent, an additive, a solvent, or the like, within a range not interfering with the effect of the present invention.

Examples of the fertilizer include compost, oil cake, fish meal, cow feces, poultry feces, or the like, or organic materials formed by processing them; nitrogen fertilizers such as ammonium sulfate, ammonium nitrate, lime nitrate, and urea; phosphoric acid fertilizers such as lime superphosphate, monoammonium phosphate, and a fused phosphorus fertilizer; potassium fertilizers such as potassium chloride, potassium sulfate, and potassium nitrate; magnesia fertilizers such as magnesia lime; lime fertilizers such as slaked lime; silicic acid fertilizers such as potassium silicate; boron fertilizers such as borate; and chemical fertilizers formed of various inorganic fertilizers.

Examples of the solid carrier include vegetable powder such as soybean flour and wheat flour; and mineral fine powder such as silicon dioxide, diatomaceous earth, apatite, gypsum, talc, bentonite, pyrophyllite, clay, and soil.

Example of the additive include organic and inorganic compounds such as sodium benzoate, urea, and mirabilite; and rapeseed oil, soybean oil, sunflower oil, castor oil, pine oil, cottonseed oil, and derivatives of these oils, and oil concentrates thereof.

Examples of the solvent include kerosene and xylene; petroleum fractions such as solvent naphtha; cyclohexane, cyclohexanone, dimethyl formamide, dimethyl sulfoxide, alcohols, acetone, methyl isobutyl ketone, mineral oils, vegetable oils, and water.

Examples of the surfactant include non-ionic surfactants such as polyoxyethylene-added alkylphenylether, polyoxyethylene-added alkylether, polyoxyethylene-added higher fatty acid ester, polyoxyethylene-added sorbitan higher fatty acid ester, polyoxyethylene-added tristyrylphenylether, sulfuric ester salts of polyoxyethylene-added alkylphenylether or the like, alkylbenzene sulfonate, sulfuric ester salts of higher alcohols or the like, alkylnaphthalene sulfonate, polycarboxylates, lignin sulfonate, alkylnaphthalene sulfonate-formaldehyde condensates, and isobutylene-maleic anhydride copolymers.

One kind or two or more kinds of other fungicides or insecticides/acaricides, and synergists may be mixed with the agricultural and horticultural fungicidal composition of the present invention so long as they do not interfere with the effects of the present invention.

Representative examples of the fungicides, insecticides, acaricides, and plant growth regulators that can be mixed and used above are shown below.

Fungicides:
Phenylamide-based: benalaxyl, benalaxyl-M, clozylacon, furalaxyl, oxadixyl, and ofurace;
Hydroxy-(2-amino)pyrimidine-based: dimethirimol and ethirimol;
N-Phenylcarbamate-based: diethofencarb;
AH fungicide (aromatic hydrocarbon)-based: biphenyl, chloroneb, dichloran, quintozene, and tecnazene;
MBI-R-based: fthalide, pyroquilon, and tricyclazole;
MBI-D-based: carpropamid, diclocymet, and fenoxanil;
Enopyranurone-based: blasticidin and mildiomycin;
Hexopyranosyl-based: kasugamycin and kasugamycin hydrochloride;
Glucopyranosyl-based: streptomycin, validamycin, and validamycin A;
Carbamate-based: idocarb, propamocarb, prothiocarb, and polycarbamate;
Uncoupling agents: binapacryl, dinocap, ferimzone, and meptyldinocap Organic tin compounds: triphenyltin acetate, triphenyltin chloride, and triphenyltin hydroxide;
Phosphate esters: phosphonic acid;
Phthalamidic acid-based: tecloftalam;
Benzotriazine-based: triazoxide;
Benzene sulfonamide-based: flusulfamide;
Tetracyclines: oxytetracycline;
Thiocarbamate-based: methasulfocarb;
Resistance inducer: acibenzolar S-methyl, probenazole, tiadinyl, and isotianil;
Other compounds: etridiazole, polyoxin, polyoxorim, oxolinic acid, hydroxyisoxazole, octhilinone, silthiofam, diflumetorim, ethaboxam, metrafenone, ferbam, metiram, propineb, zineb, ziram, dithianon, chloropicrin, dazomet, quinomethionate, ciprofuram, *agrobacterium*, and fluoroimide; isofetamid, tolprocarb, fenpyrazamine, pyriofenone, and tebufloquin; propamidine and edifenphos; and benthiazole, bethoxazin, capsaicin, carvone, cufraneb, cyprosulfamide, debacarb, dichlorophen, difenzoquat, difenzoquat-methyl sulfonate, diphenylamine, flumetover, fluoroimide, flutianil, irumamycin, methyl isothiocyanate (MITC), mildiomycin, natamycin, nitro-tar-isopropyl, oxamocarb, oxyfenthiin, propamocarb-fosetylate, propamocin-sodium, pyrimorph, pyrrolnitrin, tolnifanide, and trichlamide;

Insecticides/Acaricides, Nematocides, Soil Pesticides, and Anthelmintics:
Carbamate-based: alanycarb, aldicarb, bendiocarb, benfuracarb, carbaryl, carbofuran, carbosulfan, fenoxycarb, fenothiocarb, methiocarb, methomyl, oxamyl, pirimicarb, propoxur, thiodicarb, triazamate, ethiofencarb, fenobucarb, MIPC, MPMC, MTMC, furathiocarb, XMC, aldoxycarb, allyxycarb, aminocarb, bufencarb, butacarb, butocarboxim, butoxycarboxim, cloethocarb, dimetilan, formetanate, isoprocarb, metam-sodium, metolcarb, promecarb, thiofanox, trimethacarb, and xylycarb;
Pyrethroid-based: allethrin, bifenthrin, cyfluthrin, beta-cyfluthrin, cyhalothrin, lambda-cyhalothrin, cyphenothrin, cypermethrin, alpha-cypermethrin, beta-cypermethrin, zeta-cypermethrin, delta-methrin, esfenvalerate, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, transpermethim, empenthrin, fenfluthrin, fenpirithrin, flubrocythrinate, flufenoprox, flumethrin, metofluthrin, phenothrin, protrifenbute, pyresmethrin, and terallethrin;

Growth Regulators:
(a) Chitin synthesis inhibitors: chlorfluazuron, diflubenzuron, flucycloxuron, flufenoxuron, hexaflumuron, lufenuron, novaluron, teflubenzuron, triflumuron, bistrifluoron, noviflumuron, etoxazole, clofentezine, fluazuron, and penfluoron;
(b) Ecdysone antagonists: halofenozide, methoxyfenozide, chromafenozide, and azadirachtin;
(c) Juvenile hormone-like substances: pyriproxyfen, methoprene, diofenolan, epofenonane, hydroprene, kinoprene, and triprene; and
(d) Lipid biosynthesis inhibitors: spirodiclofen, spiromesifen, spirotetramat, and flonicamid;

Nicotine Receptor Agonist/Antagonist Compounds: nicotine, bensultap, cartap, and flupyradifurone;

GABA Antagonist Compounds:
(a) Acetoprole, vaniliprole, pyrafluprole, pyriprole; and
(b) Organochlorine-based: camphechlore, chlordane, endosulfan, HCH, γ-HCH, heptachlor, and methoxychlor;

Macrocyclic lactone insecticides: abamectin, emamectin benzoate, milbemectin, lepimectin, ivermectin, seramectin, doramectin, epinomectin, moxidectin, milbemycin, and milbemycin oxime;

METI I compounds: fenazaquin, pyridaben, tebufenpyrad, tolfenpyrad, flufenerim, hydramethylnon, fenpyroximate, pyrimidifen, and dicofol;

METI II and III compounds: acequinocyl, fluacrypyrim, and rotenone;

Uncoupling agent compounds: binapacryl, dinobuton, dinocap, and DNOC; Oxidative phosphorylation inhibitor compounds: cyhexatin, diafenthiuron, fenbutatin oxide, propargite, and azocyclotin;

Molting disruption compounds: cyromazine;

Mixed function oxidase inhibitor compounds: piperonyl butoxide;

Sodium channel blocker compounds: indoxacarb and metaflumizone;

Microbial pesticides: BT agents, insect pathogen viral agents, insect pathogen fungal agents, nematode pathogen fungal agents; *bacillus, beauveria bassiana, metarhizium anisopliae, paecilomyces, thuringiensin*, and *verticillium;*

Latrophilin receptor agonists: depsipeptide, cyclodepsipeptide, 24-membered cyclodepsipeptide, and emodepside;

Octopamine agonists: amitraz;

Ryanodine receptor agonists: flubendiamide, chlorantraniliprole, and cyantraniliprole;

Magnesium-stimulated ATPase inhibitors: thiocyclam, thiosultap, and nereistoxin;

Acari growth inhibitors: clofentezine and etoxazole;

Other compounds: benclothiaz, bifenazate, pyridalyl, sulfur, cyenopyrafen, cyflumetofen, amidoflumet, tetradifon, chlordimeform, 1,3-dichloropropene, DCIP, phenisobromolate, benzomate, methaldehyde, spinetoram, pyrifluquinazon, benzoxymate, bromopropylate, quinomethionate, chlorobenzilate, chloropicrin, chlothiazoben, dicyclanil, fenoxacrim, fentrifanil, flubenzimine, fluphenzine, gossyplure, japonilure, metoxadiazone, petroleum, potassium oleate, sulfluramid, tetrasul, and triarathene; afidopyropen, pyflubumide, flometoquin, flufiprole, fluensulfone, meperfluthrin, tetramethylfluthrin, sulfoxaflor, imicyafos, tralopyril, diflovidazin, dimefluthrin, and methylneodecanamide;

Anthelmintics:
(a) benzimidazole-based: fenbendazole, albendazole, triclabendazole, and oxybendazole;
(b) salicylanilide-based: closantel and oxyclozanide;
(c) substituted phenol-based: nitroxinil;
(d) pyrimidine-based: pyrantel;
(e) imidazothiazole-based: levamisole;
(f) tetrahydropyrimidine: praziquantel; and
(g) other anthelmintic drugs: cyclodiene, ryania, clorsulon, metronidazole, and demiditraz;

Plant Growth Regulators:
abscisic acid, indole butyric acid, uniconazole, ethychlozate, ethephon, cloxyfonac, chlormequat, a *chlorella* extract, calcium peroxide, cyanamide, dichlorprop, gibberellin, daminozide, decyl alcohol, trinexapac-ethyl, mepiquat-chloride, paclobutrazol, paraffin wax, piperonyl butoxide, pyraflufen-ethyl, flurprimidol, prohydrojasmon, a prohexadione-calcium salt, benzylaminopurine, pendimethalin, forchlorfenuron, potassium hydrazide maleate, 1-naphthylacetoamide, 4-CPA, MCPB, choline, oxyquinoline sulfate, ethychlozate, butralin, 1-methylcyclopropene, and aviglycine hydrochloride.

The formulation obtained by formulating the compound A, the compound B, or a mixture thereof into a preparation is not particularly limited, and may adopt a form able to be adopted by ordinary agricultural and horticultural chemicals, for example, powder, a wettable powder, a soluble powder, an emulsifiable concentrate, a flowable agent, wettable granules, granules, or the like.

The concentration of the active ingredient (the total concentration of the compound A and the compound B) in the fungicidal composition of the present invention, which has been formulated into a preparation, is not particularly limited and various concentrations can be adopted according to the forms of the preparations above. For example, for wettable powders, the concentration of the active ingredient may be usually 5% by weight to 90% by weight, and preferably 10% by weight to 85% by weight; for emulsifiable concentrates, the concentration of the active ingredient may be usually 3% by weight to 70% by weight, and preferably 5% by weight to 60% by weight; and for granules, the concentration of the active ingredient may be usually 0.01% by weight to 50% by weight, and preferably 0.05% by weight to 40% by weight.

The fungicidal composition of the present invention, which has been formulated into a preparation, is diluted as it is or at a predetermined concentration with water, and thus, it is used by spraying to plants, or irrigating, incorporating, or spraying to soil, in the form of a solution, a suspension, or an emulsion. When the fungicidal composition of the present invention is subjected to an agricultural field, a suitable amount of 0.1 g or more (as a compound total amount with the compound A and the B) of an active ingredient per hectare is usually used.

Examples of useful plants to be treated in the fungicidal composition of the present invention include cereals, vegetables, root vegetables, potatoes, trees, grasses, and lawn. In this case, each part of these plants may be subjected to the treatment. Examples of the part of the plants include leaves, stems, florals, flowers, buds, fruits, seeds, sprouts, roots, tubers, tuberous roots, shoots, and cuttings. It is also possible to subject the improved varieties/variants of these plants, and cultivars, mutants, hybrid bodies, or genetically modified bodies (GMO) to the treatment.

An example of the useful plants is shown below.

(1) Malvaceae plants, for example, okra (*Abelmoschus esculentus*) and cotton (*Gossypium hirsutum*);

(2) Sterculiaceae plants, for example, cacao (*Theobroma cacao*);

(3) Chenopodiaceae plants, for example, sugar beet (*Beta vulgaris*), Swiss chard (*Beta vulgaris* var. *cicla* L.), and spinach (*Spinacia oleracea*);

(4) Rubiaceae plants, for example, coffee (*Coffea* spp);

(5) Cannabaceae plants, for example, hop (*Humulus lupulus*)

(6) Cruciferae plants, for example, komatsuna (*Brassica cempestris*), mustard (*Brassica juncea*), tacana (*Brassica juncea* var. *integrifolia*), rape (*Brassica napus*), cauliflower (*Brassica oleracea* var. *botrytis*), cabbage (*Brassica oleracea* var. *capitata*), broccoli (*Brassica oleracea* var. *italica*), Chinese cabbage (*Brassica rapa*), bok choy (*Brassica rapa* var. *chinensis*), turnip (*Brassica rapa* var. *glabra*), Nozawana (*Brassica rapa* var. *hakabura*), mizuna (*Brassica rapa* var. *lancinifolia*), Shepherd's purse (*Capsella bursa-pastoris*), watercress (*Nasturtium* spp.), radish (*Raphanus sativus*), and wasabi (*Wasabia japonica*);

(7) Linaceae plants, for example, flax (*Linaceae usitatissimum*);

(8) Gramineae plants, for example, oat (*Avena sativa*), Job's tears (*Coix lacryma-jobi* var. *ma-yuen*), orchardgrass (*Dactylis glomerata*), barley (*Hordeum vulgare*), rice (*Oryza sativa*), timothy (*TPhleum pratense*), sugar cane (*Saccha-* rum officinarum), rye (Secale cereale), millet (Setaria italica), bread wheat (Triticum aestivum), corn (Zea meys), and zoysiagrass (Zoysia spp.);

(9) Cucurbitaceae plants, for example, wax gourd (Benincasa hispida), watermelon (Citrulus lanatus), bittercup squash (Cucurbita maxima), Oriental pumpkin (Cucurbita moschata), cucurbita pepo (zucchini) (Cucurbita pepo), gourd (Lagenaria siceraria), and sponge gourd (Luffa cylindrica);

(10) Anacardiaceae plants, for example, cashew (Anacardium) and mango (Mangifera);

(11) Ebenaceae plants, for example, diospyros (Diospyros kaki);

(12) Betulaceae plants, for example, hazel (Corylus avellana);

(13) Compositae plants, for example, wormwood (Artemisia indica var. maximowiczii), burdock (Arctium lappa L.), chicory (Cichorium intybus), artichoke (Cynara scolymus), crown daisy (Glebionis coronaria), sunflower (Helianthus annuus), and lettuce (Lactuca sativa);

(14) Asparagaceae plants, for example, asparagus (Asparagus officinalis L.);

(15) Moraceae plants, for example, fig (Ficus carica L.);

(16) Juglandaceae plants, for example, walnut (Juglans spp.);

(17) Pedaliaceae plants, for example, sesame (Sesamum indicum);

(18) Piperaceae plants, for example, pepper (Piper nigrum);

(19) Araceae plants, for example, konjac (Amorphophallus rivieri var. konjac) and taro (Colocasia esculenta);

(20) Lamiaceae plants, for example, peppermint (mint) (Mentha spp.), basil (Ocimum basilicum), perilla (Perilla frutescens var. crispa), and sage (Salvia officinalis);

(21) Zingiberaceae plants, for example, turmeric (Curcuma longa), ginger (Hedychium spp.), and myoga (Zingiber mioga);

(22) Umbelliferae plants, for example, celery (Apium graveolens L.), carrot (Daucus carota var. sativa), seri (Oenanthe javanica), royal fern (Osmunda japonica Thunb), and parsely (Petroselium crispum);

(23) Grossulariaceae plants, for example, Western currant (gooseberry) (Ribes uva-crispa);

(24) Polygonaceae plants, for example, buckwheat (Fagopyrum esculentum);

(25) Ericaceae plants, for example, blueberries (Vaccinium spp);

(26) Theaceae plants, for example, tea plant (Camellia sinensis);

(27) Solanaceae plants, for example, pepper (Capsicum annuum), bell pepper (Capsicum annuum var. 'grossum'), tomato (Lycopersicon esculentum), tobacco (Nicotiana tabacum), eggplant (Solanum melongena), and potato (Solanum tuberosum);

(28) Bromeliaceae plants, for example, pineapple (Ananas comosus);

(29) Musaceae plants, for example, banana (Musa spp.);

(30) Nelumbonaceae plants, for example, lotus (Nelumbo nucifera)

(31) Caricaceae plants, for example, papaya (Carica papaya)

(32) Rosaceae plants, for example, quince (Chaenomeles sinensis), loquat (Eriobotrya japonica Lindl.), strawberry (Fragaria spp.), apple (Malus pumila), apricot (Prunus armeniaca), sweet cherry (Prunus avium), sour cherry (Prunus cerasus), almonds (Prunus dulcis), plum (Prunus mume), peach (Prunus persica), plum (Prunus salicina), pear (Pyrus pyrifolia var. culta), European pear (Pyrus communis), and blackberry (Rubus spp.);

(33) Convolvulaceae plants, for example, sweet potato (Ipomoea batatas Lam. var. edulis Makino);

(34) Vitaceae plants, for example, grape (Vitis spp.);

(35) Fagaceae plants, for example, chestnut (Castanea crenata Sieb. Et Zucc.);

(36) Actinidiaceae plants, for example, kiwi (Actinidia deliciosa);

(37) Leguminosae plants, for example, peanut (Arachis hypogaea), soybean (Glycine max subsp. max), glycine soja (Glycine max subsp. soja), lentil (Lens culinaris), alfalfa (Medicago sativa), pea legume (Pisum sativum L.), common bean (Phaseolus vulgaris), narrow-leaved vetch (Vicia angustifolia), broad bean (Vicia faba), and adzuki bean (Vigna angularis);

(38) Rutaceae plants, for example, yuzu (Citrus junos), komikan (Kishu mandarin) (Citrus kinokuni), lemon (Citrus limon), orange (Citrus sinensis), satsuma mandarin (Citrus unshiu), grapefruit (Citrus X paradisi), Kumquat (Fortunella japonica), and Japanese pepper (Zanthoxylum piperitum);

(39) Oleaceae plants, for example, jasmine (Jasminum spp.) and olive (Olea europaea);

(40) Dioscoreaceae plants, for example, Taiwanese yam (Dioscorea japonica Thunb.) and yam (Dioscorea batatas);

(41) Liliaceae plants, for example, onion (Allium cepa), leek (Allium fistulosum), garlic (Allium sativum), chives (Allium schoenoprasum), Chinese chive (Allium tuberosum), and tulip (Tulipa gesneriana);

The fungicidal composition of the present invention has an excellent fungicidal power for a wide variety of filamentous fungi, for example, fungi belong to algae fungi (Oomycetes), sac fungi (Ascomycetes), imperfect fungi (Deuteromycetes), or Basidiomycete fungi (Basidiomycetes).

The fungicidal composition of the present invention can be in control of various diseases generated upon cultivation of agricultural and horticultural crops, including flowers, lawn, and glasses by seed treatment, foliar spray, soil application, water application, or the like.

The fungicidal composition of the present invention can be used for the control of problems with:

sugar beets: Cercospora leaf spot (Cercospora beticola), Aphanomyces root rot (Aphanomyces cochlioides), root rot (Thanatephorus cucumeris), and Leaf blight (Thanatephorus cucumeris);

peanuts: brown leaf spot (Mycosphaerella arachidis) and leaf spot (Mycosphaerella berkeleyi);

cucumbers: powdery mildew (Sphaerotheca fuliginea), downy mildew (Pseudoperonospora cubensis), gummy stem blight (Mycosphaerella melonis), Fusarium wilt (Fusarium oxysporum), Sclerotinia rot (Sclerotinia sclerotiorum), gray mold (Botrytis cinerea), anthracnose (Colletotrichum obriculare), scab (Cladosporium cucumerinum), Corynespora leaf spot (Corynespora cassicola), damping-off (Pythium debaryanam, Rhizoctonia solani Kuhn), and bacterial spot (Pseudomonas syringae pv. Lecrymans);

tomatoes: gray mold (Botrytis cinerea), leaf mold (Cladosporium fulvum), and late blight (Phytophthora infestans);

eggplants: gray mold (Botrytis cinerea), black rot (Corynespora melongenae), powdery mildew (Erysiphe cichoracearum), and leaf mold (Mycovellosiella nattrassii);

strawberries: gray mold (Botrytis cinerea), powdery mildew (Sohaerotheca humuli), anthracnose (Colletotrichum acutatum, Colletotrichum fragariae), and Phytophthora rot (Phytophthora cactorum);

onions: neck rot (*Botrytis allii*), gray mold (*Botrytis cinerea*), leaf blight (*Botrytis squamosa*), and downy mildew (*Peronospora destructor*);

cabbage: clubroot (*Plasmodiophora brassicae*), bacterial soft rot (*Erwinia carotovora*), and downy mildew (*Peronospora parasitica*);

kidney beans: stem rot (*Sclerotinia sclerotiorum*) and gray mold (*Botrytis cinerea*);

apples: powdery mildew (*Podosphaera leucotricha*), scab (*Venturia inaequalis*), blossom blight (*Monilinia mali*), fruit spot (*Mycosphaerella pomi*), valsa canker (*Valsa mali*), Alternaria blotch (*Alternaria mali*), rust (*Gymnosporangium yamadae*), ring rot (*Botryosphaeria berengeriana*), anthracnose (*Glomerella cingulata, Colletotrichum acutatum*), blotch (*Diplocarpon mali*), fly speck (*Zygophiala jamaicensis*), and sooty blotch (*Gloeodes pomigena*);

persimmons: powdery mildew (*Phyllactinia kakicola*), anthracnose (*Gloeosporium kaki*), and angular leaf spot (*Cercospora kaki*);

peaches: brown rot (*Monilinia fructicola*), scab (*Cladosporium carpophilum*), and *Phomopsis* rot (*Phomopsis* sp.);

cherries: brown rot (*Monolinia fructicola*);

grapes: gray mold (*Botrytis cinerea*), powdery mildew (*Uncinula necator*), ripe rot (*Glomerella cingulata, Colletotrichum* acutatum), downy mildew (*Plasmopara viticola*), anthracnose (*Elsinoe ampelina*), leaf blight (*Pseudocercospora vitis*), and black rot (*Guignardia bidwellii*);

pears: scab (*Venturia nashicola*), rust (*Gymnosporangium asiaticum*), black spot (*Alternaria kikuchiana*), ring rot (*Botryosphaeria berengeriana*), and powdery mildew (*Phyllactinia mali*);

tea: gray blight (*Pestalotia theae*) and anthracnose (*Collectotrichum theae-sinensis*);

citrus: scab (*Elsinoe fawcetti*), blue mold (*Penicillium italicum*), common green mold (*Penicillium digitatum*), gray mold (*Botrytis cinerea*), melanose (*Diaporthe citri*), and canker (*Xanthomonas campestris* pv. *Citri*);

wheat: powdery mildew (*Erysiphe graminis* f sp. *tritici*), fusarium blight (*Gibberella zeae*), leaf rust (*Puccinia recondita*), browning root rot (*Pythium iwayamai*), snow mold (*Monographella nivalis*), eye spot (*Pseudocercosporella herpotrichoides*), speckled leaf blotch (*Septoria tritici*), glume blotch (*Leptosphaeria nodorum*), typhula snow blight (*Typhula incarnata*), sclerotinia snow blight (*Myrosclerotinia borealis*), and take-all (*Gaeumanomyces graminis*);

barley: stripe (*Pyrenophora graminea*), leaf blotch (*Rhynchosporium secalis*), and loose smut (*Ustilago tritici, U. nuda*);

rice: blast (*Pyricularia oryzae*), sheath blight (*Rhizoctonia solani*), bakanae disease (*Gibberella fujikuroi*), brown spot (*Cochliobolus niyabeanus*), seedling blight (*Pythium graminicolum*), bacterial leaf blight (*Xanthomonas oryzae*), bacterial seedling blight (*Burkholderia plantarii*), bacterial brown stripe (*Acidovorax avanae*), and bacterial grain rot (*Burkholderia glumae*);

tobacco: *Sclerotinia* stem-rot (*Sclerotinia sclerotiorum*) and powdery mildew (*Erysiphe cichoracearum*);

tulips: gray mold (*Botrytis cinerea*);

bent grass: *Sclerotinia* snow blight (*Sclerotinia borealis*) and bacterial shoot blight (*Pythium aphanidermatum*);

orchard grass: powdery mildew (*Erysiphe graminis*);

soybeans: purple stain (*Cercospora kikuchii*), downy mildew (*Peronospora Manshurica*), and *Phytophthora* root and stem rot (*Phytophthora sojae*);

potatoes/tomatoes: late blight (*Phytophthora infestans*); and the like.

Furthermore, the fungicidal composition of the present invention has an excellent fungicidal effect even on resistant fungi. Further, since the fungicidal composition exhibits the effect even when used at very low doses, it has an effect of preventing the emergence of new resistant fungi.

Examples of diseases for which the application of the fungicidal composition of the present invention is more preferable include scab of apples, gray mold disease of cucumbers, powdery mildew of wheat, late blight of tomato, leaf rust of wheat, rice blast, and vine wilt of cucumbers.

EXAMPLES

Next, the present invention will be described in more detail with reference to Examples. However, the present invention is not limited to Examples in any way.

Example 1 and Comparative Example 1

The drug I and the drug II were dissolved in dimethyl sulfoxide separately at the concentrations shown in Tables 1 to 5. The solutions thus obtained were mixed to prepare fungicidal compositions.

Additionally, in Tables, the symbol A indicating the drug I represents a nitrogen-containing heterocyclic compound represented by the formula (A), the symbol B indicating the drug I represents a nitrogen-containing heterocyclic compound represented by the formula (B), and the symbol C indicating the drug I represents a nitrogen-containing heterocyclic compound represented by the formula (C). Further, in Tables, the number indicating the drug II represents each of the compounds [1] to [61] described below. Additionally, "-" in Tables represents that the drug was not used.

[Chem. 20]

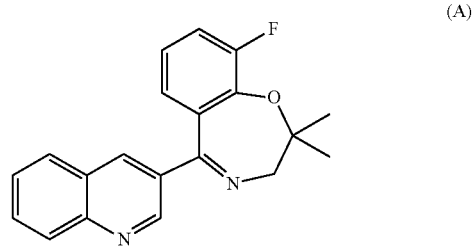

(A)

[Chem. 21]

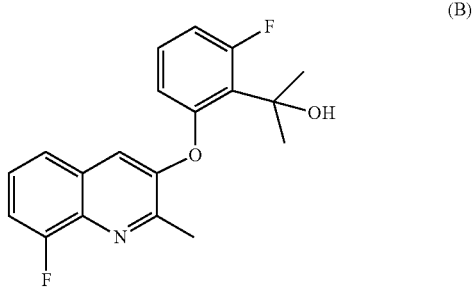

(B)

-continued

[Chem. 22]

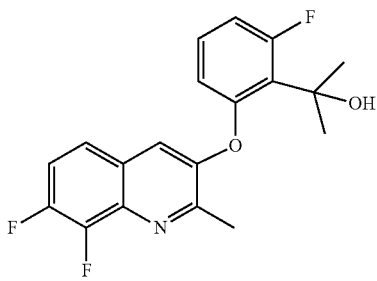

[1] Cyflufenamid
[2] Triflumizole
[3] Thiophanate-methyl
[4] Iminoctadine acetate
[5] Iminoctadine albesilate
[6] Metalaxyl
[7] Cymoxanil
[8] Benthiavalicarb-isopropyl
[9] Famoxadone
[10] Ametoctradin
[11] Fluopicolide
[12] Zoxamide
[13] Fosetyl
[14] Cyazofamid
[15] Proquinazid
[16] Metrafenone
[17] Quinoxifen
[18] Flutolanil
[19] Diclomezin
[20] Fludioxonil
[21] Difenoconazole
[22] Tebuconazole
[23] Carboxin
[24] Thiram
[25] Chlorothalonil
[26] Trifloxystrobin
[27] Azoxystrobin
[28] Kresoxim-methyl
[29] Pyribencarb
[30] Fluopyram
[31] Fluazinam
[32] Manzeb
[33] Captan
[34] Cyprodinil
[35] Tolclofos-methyl
[36] Iprodione
[37] Folpet
[38] Compound represented by the formula (20)
[39] Compound represented by the formula (21)

[Chem. 23]

(20)

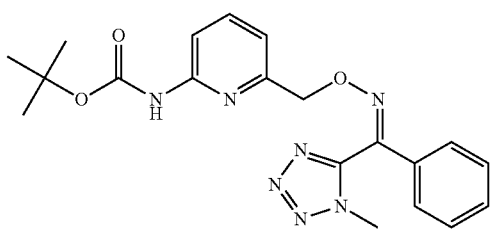

-continued

[Chem. 24]

(C)

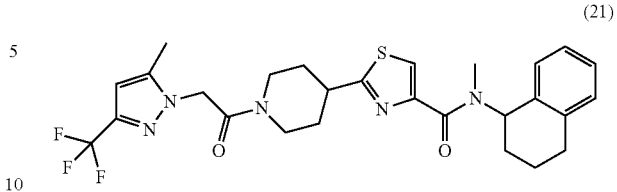

(21)

[40] Orysastrobin
[41] Isoprothiolane
[42] Acetamiprid
[43] Hexythiazox
[44] Tebufenozide
[45] Imidacloprid
[46] Thiamethoxam
[47] Clothianidin
[48] Chlorpyrifos
[49] Thiodicarb
[50] Spinosad
[51] Dinotefuran
[52] Etofenprox
[53] Fipronil
[54] Ethiprole
[55] Pymetrozine
[56] Thifluzamide
[57] Buprofezin
[58] Boscalid
[59] Chlorfenapyr
[60] Bupirimate
[61] Compound represented by the formula (22)

[Chem. 25]

(22)

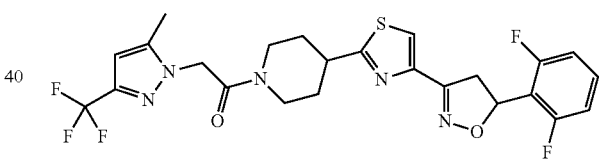

(Sterilization Test)

Conidia of *Botrytis cinerea* were added to and dispersed in a potato dextrose culture medium. A fungicidal composition was added thereto and mixed. This was dispensed in a 96-well microplate and cultured at 20° C. for 3 days in a dark setting. Then, the turbidity was measured at a wavelength of 405 nm in a microplate reader. From comparison with the measured value of turbidity in the case of non-treatment (without the addition of the fungicidal composition), the growth inhibition rate of *Botrytis cinerea* (%) was calculated. The test was carried out in duplicate. Further, the expected value of the growth inhibition was calculated based on Colby's equation. The results thereof are shown in Tables 1 to 5.

In addition, the Colby's equation is E=M+N−MN/100. Here, E is the expected value of a growth inhibition rate (%), M is the growth inhibition rate (%) calculated from the measurement with the use of the drug I alone, and N is the growth inhibition rate (%) calculated from the measurement with the use of the drug II alone. Additionally, in Tables, the expected values with the use of the drug alone were not shown, because they were the same as the values calculated from the measurement.

TABLE 1

| Drug I | | Drug II | | Growth inhibition rate | Expected value |
|---|---|---|---|---|---|
| Type | Concentration (ppm) | Type | Concentration (ppm) | (%) | (%) |
| A | 0.1 | 1 | 10 | 59 | 27 |
| B | 0.1 | 1 | 10 | 53 | 27 |
| C | 0.1 | 1 | 10 | 59 | 26 |
| — | — | 1 | 10 | 9 | — |
| A | 0.1 | 2 | 2 | 88 | 66 |
| B | 0.1 | 2 | 2 | 82 | 67 |
| C | 0.1 | 2 | 2 | 85 | 66 |
| — | — | 2 | 2 | 59 | — |
| A | 0.1 | 3 | 0.02 | 23 | 19 |
| B | 0.1 | 3 | 0.02 | 24 | 19 |
| C | 0.1 | 3 | 0.02 | 24 | 19 |
| — | — | 3 | 0.02 | 0 | — |
| A | 0.1 | 4 | 0.02 | 65 | 41 |
| B | 0.1 | 4 | 0.02 | 53 | 41 |
| C | 0.1 | 4 | 0.02 | 61 | 41 |
| — | — | 4 | 0.02 | 27 | — |

TABLE 2

| Drug I | | Drug II | | Growth inhibition rate | Expected value |
|---|---|---|---|---|---|
| Type | Concentration (ppm) | Type | Concentration (ppm) | (%) | (%) |
| A | 0.1 | 5 | 0.02 | 44 | 24 |
| B | 0.1 | 5 | 0.02 | 40 | 24 |
| C | 0.1 | 5 | 0.02 | 47 | 24 |
| — | — | 5 | 0.02 | 6 | — |
| A | 0.1 | 6 | 10 | 26 | 19 |
| B | 0.1 | 6 | 10 | 23 | 19 |
| C | 0.1 | 6 | 10 | 25 | 19 |
| — | — | 6 | 10 | 0 | — |
| A | 0.1 | 7 | 2 | 31 | 19 |
| B | 0.1 | 7 | 2 | 28 | 19 |
| C | 0.1 | 7 | 2 | 27 | 19 |
| — | — | 7 | 2 | 0 | — |
| A | 0.1 | 8 | 10 | 26 | 19 |
| B | 0.1 | 8 | 10 | 30 | 19 |
| C | 0.1 | 8 | 10 | 34 | 19 |
| — | — | 8 | 10 | 0 | — |
| A | 0.1 | 9 | 2 | 27 | 19 |
| B | 0.1 | 9 | 2 | 30 | 19 |
| C | 0.1 | 9 | 2 | 30 | 19 |
| — | — | 9 | 2 | 0 | — |
| A | 0.1 | 10 | 10 | 52 | 19 |
| B | 0.1 | 10 | 10 | 51 | 19 |
| C | 0.1 | 10 | 10 | 57 | 19 |
| — | — | 10 | 10 | 0 | — |
| A | 0.1 | 11 | 10 | 34 | 24 |
| B | 0.1 | 11 | 10 | 39 | 24 |
| C | 0.1 | 11 | 10 | 38 | 24 |
| — | — | 11 | 10 | 6 | — |
| A | 0.1 | 12 | 0.4 | 56 | 21 |
| B | 0.1 | 12 | 0.4 | 57 | 21 |
| C | 0.1 | 12 | 0.4 | 61 | 21 |
| — | — | 12 | 0.4 | 3 | — |
| A | 0.1 | 13 | 0.08 | 24 | 20 |
| B | 0.1 | 13 | 0.08 | 31 | 21 |
| C | 0.1 | 13 | 0.08 | 27 | 20 |
| — | — | 13 | 0.08 | 2 | — |

TABLE 3

| Drug I | | Drug II | | Growth inhibition rate | Expected value |
|---|---|---|---|---|---|
| Type | Concentration (ppm) | Type | Concentration (ppm) | (%) | (%) |
| A | 0.1 | 14 | 10 | 94 | 19 |
| B | 0.1 | 14 | 10 | 91 | 19 |

TABLE 3-continued

| Drug I | | Drug II | | Growth inhibition rate (%) | Expected value (%) |
|---|---|---|---|---|---|
| Type | Concentration (ppm) | Type | Concentration (ppm) | | |
| C | 0.1 | 14 | 10 | 94 | 19 |
| — | — | 14 | 10 | 0 | — |
| A | 0.1 | 15 | 10 | 57 | 19 |
| B | 0.1 | 15 | 10 | 62 | 19 |
| C | 0.1 | 15 | 10 | 69 | 19 |
| — | — | 15 | 10 | 0 | — |
| A | 0.1 | 16 | 10 | 35 | 19 |
| B | 0.1 | 16 | 10 | 42 | 19 |
| C | 0.1 | 16 | 10 | 44 | 19 |
| — | — | 16 | 10 | 0 | — |
| A | 0.1 | 17 | 2 | 48 | 19 |
| B | 0.1 | 17 | 2 | 45 | 19 |
| C | 0.1 | 17 | 2 | 53 | 19 |
| — | — | 17 | 2 | 0 | — |
| A | 0.1 | 18 | 10 | 57 | 19 |
| B | 0.1 | 18 | 10 | 57 | 19 |
| C | 0.1 | 18 | 10 | 62 | 19 |
| — | — | 18 | 10 | 0 | — |
| A | 0.1 | 19 | 10 | 45 | 19 |
| B | 0.1 | 19 | 10 | 43 | 19 |
| C | 0.1 | 19 | 10 | 43 | 19 |
| — | — | 19 | 10 | 0 | — |
| A | 0.1 | 20 | 0.02 | 71 | 51 |
| B | 0.1 | 20 | 0.02 | 68 | 51 |
| C | 0.1 | 20 | 0.02 | 76 | 51 |
| — | — | 20 | 0.02 | 39 | — |
| A | 0.1 | 21 | 0.4 | 83 | 48 |
| B | 0.1 | 21 | 0.4 | 71 | 48 |
| C | 0.1 | 21 | 0.4 | 77 | 48 |
| — | — | 21 | 0.4 | 36 | — |
| A | 0.1 | 22 | 0.08 | 75 | 47 |
| B | 0.1 | 22 | 0.08 | 64 | 47 |
| C | 0.1 | 22 | 0.08 | 68 | 47 |
| — | — | 22 | 0.08 | 34 | — |

TABLE 4

| Drug I | | Drug II | | Growth inhibition rate (%) | Expected value (%) |
|---|---|---|---|---|---|
| Type | Concentration (ppm) | Type | Concentration (ppm) | | |
| A | 0.1 | 23 | 0.4 | 67 | 19 |
| B | 0.1 | 23 | 0.4 | 58 | 19 |
| C | 0.1 | 23 | 0.4 | 61 | 19 |
| — | — | 23 | 0.4 | 0 | — |
| A | 0.1 | 24 | 0.08 | 58 | 44 |
| B | 0.1 | 24 | 0.08 | 51 | 44 |
| C | 0.1 | 24 | 0.08 | 56 | 43 |
| — | — | 24 | 0.08 | 30 | — |
| A | 0.1 | 25 | 0.08 | 72 | 22 |
| B | 0.1 | 25 | 0.08 | 63 | 23 |
| C | 0.1 | 25 | 0.08 | 66 | 22 |
| — | — | 25 | 0.08 | 4 | — |
| A | 0.1 | 26 | 0.08 | 91 | 45 |
| B | 0.1 | 26 | 0.08 | 87 | 45 |
| C | 0.1 | 26 | 0.08 | 89 | 45 |
| — | — | 26 | 0.08 | 32 | — |
| A | 0.1 | 27 | 0.08 | 73 | 43 |
| B | 0.1 | 27 | 0.08 | 68 | 43 |
| C | 0.1 | 27 | 0.08 | 67 | 43 |
| — | — | 27 | 0.08 | 30 | — |
| A | 0.1 | 28 | 0.08 | 90 | 35 |
| B | 0.1 | 28 | 0.08 | 85 | 35 |
| C | 0.1 | 28 | 0.08 | 88 | 35 |
| — | — | 28 | 0.08 | 20 | — |
| A | 0.1 | 29 | 0.02 | 72 | 37 |
| B | 0.1 | 29 | 0.02 | 74 | 37 |
| C | 0.1 | 29 | 0.02 | 80 | 36 |
| — | — | 29 | 0.02 | 22 | — |
| A | 0.1 | 30 | 0.08 | 52 | 32 |
| B | 0.1 | 30 | 0.08 | 43 | 33 |
| C | 0.1 | 30 | 0.08 | 50 | 32 |
| — | — | 30 | 0.08 | 16 | — |
| A | 0.1 | 31 | 0.02 | 45 | 35 |
| B | 0.1 | 31 | 0.02 | 43 | 35 |
| C | 0.1 | 31 | 0.02 | 50 | 35 |
| — | — | 31 | 0.02 | 20 | — |

TABLE 5

| Drug I | | Drug II | | Growth inhibition rate | Expected value |
|---|---|---|---|---|---|
| Type | Concentration (ppm) | Type | Concentration (ppm) | (%) | (%) |
| A | 0.1 | 32 | 2 | 78 | 28 |
| B | 0.1 | 32 | 2 | 71 | 28 |
| C | 0.1 | 32 | 2 | 70 | 28 |
| — | — | 32 | 2 | 11 | — |
| A | 0.1 | 33 | 0.02 | 56 | 42 |
| B | 0.1 | 33 | 0.02 | 60 | 42 |
| C | 0.1 | 33 | 0.02 | 56 | 41 |
| — | — | 33 | 0.02 | 28 | — |
| A | 0.1 | 34 | 0.02 | 29 | 19 |
| B | 0.1 | 34 | 0.02 | 22 | 19 |
| C | 0.1 | 34 | 0.02 | 25 | 19 |
| — | — | 34 | 0.02 | 0 | — |
| A | 0.1 | 35 | 10 | 72 | 48 |
| B | 0.1 | 35 | 10 | 75 | 48 |
| C | 0.1 | 35 | 10 | 80 | 48 |
| — | — | 35 | 10 | 35 | — |
| A | 0.1 | 36 | 0.4 | 73 | 50 |
| B | 0.1 | 36 | 0.4 | 75 | 50 |
| C | 0.1 | 36 | 0.4 | 69 | 50 |
| — | — | 36 | 0.4 | 39 | — |
| A | 0.1 | 37 | 0.02 | 38 | 27 |
| B | 0.1 | 37 | 0.02 | 30 | 27 |
| C | 0.1 | 37 | 0.02 | 45 | 27 |
| — | — | 37 | 0.02 | 10 | — |
| A | 0.1 | 38 | 10 | 48 | 26 |
| B | 0.1 | 38 | 10 | 43 | 27 |
| C | 0.1 | 38 | 10 | 47 | 26 |
| — | — | 38 | 10 | 9 | — |
| A | 0.1 | 39 | 10 | 39 | 29 |
| B | 0.1 | 39 | 10 | 40 | 30 |
| C | 0.1 | 39 | 10 | 51 | 29 |
| — | — | 39 | 10 | 13 | — |
| A | 0.1 | — | — | 19 | — |
| B | 0.1 | — | — | 19 | — |
| C | 0.1 | — | — | 19 | — |

Example 2 and Comparative Example 2

At the concentrations shown in Tables 6 to 8, the drug I and the drug II were dissolved separately in dimethyl sulfoxide. The obtained solution was mixed to prepare a fungicidal composition.

Using the same methods as in Example 1 and Comparative Example 1, the sterilization test was carried out. The results thereof are shown in Tables 6 to 8. Additionally, in Tables, the expected values with the use of the drug alone were not shown, because they were the same as the values calculated from the measurement.

TABLE 6

| Drug I | | Drug II | | Growth inhibition rate | Expected value |
|---|---|---|---|---|---|
| Type | Concentration (ppm) | Type | Concentration (ppm) | (%) | (%) |
| A | 0.1 | 40 | 10 | 93 | 66 |
| B | 0.1 | 40 | 10 | 92 | 65 |
| C | 0.1 | 40 | 10 | 92 | 66 |
| — | — | 40 | 10 | 58 | — |
| A | 0.1 | 41 | 10 | 51 | 28 |
| B | 0.1 | 41 | 10 | 38 | 27 |
| C | 0.1 | 41 | 10 | 47 | 29 |
| — | — | 41 | 10 | 10 | — |

TABLE 7

| Drug I | | Drug II | | Growth inhibition rate (%) | Expected value (%) |
|---|---|---|---|---|---|
| Type | Concentration (ppm) | Type | Concentration (ppm) | | |
| A | 0.1 | 42 | 10 | 24 | 20 |
| B | 0.1 | 42 | 10 | 22 | 18 |
| C | 0.1 | 42 | 10 | 30 | 21 |
| — | — | 42 | 10 | 0 | — |
| A | 0.1 | 43 | 10 | 31 | 20 |
| B | 0.1 | 43 | 10 | 32 | 18 |
| C | 0.1 | 43 | 10 | 32 | 21 |
| — | — | 43 | 10 | 0 | — |
| A | 0.1 | 44 | 10 | 48 | 20 |
| B | 0.1 | 44 | 10 | 36 | 18 |
| C | 0.1 | 44 | 10 | 39 | 21 |
| — | — | 44 | 10 | 0 | — |
| A | 0.1 | 45 | 10 | 23 | 20 |
| B | 0.1 | 45 | 10 | 26 | 18 |
| C | 0.1 | 45 | 10 | 27 | 21 |
| — | — | 45 | 10 | 0 | — |
| A | 0.1 | 46 | 10 | 27 | 20 |
| B | 0.1 | 46 | 10 | 28 | 18 |
| C | 0.1 | 46 | 10 | 37 | 21 |
| — | — | 46 | 10 | 0 | — |
| A | 0.1 | 47 | 10 | 30 | 23 |
| B | 0.1 | 47 | 10 | 27 | 21 |
| C | 0.1 | 47 | 10 | 30 | 24 |
| — | — | 47 | 10 | 4 | — |
| A | 0.1 | 48 | 10 | 33 | 20 |
| B | 0.1 | 48 | 10 | 35 | 18 |
| C | 0.1 | 48 | 10 | 31 | 21 |
| — | — | 48 | 10 | 0 | — |
| A | 0.1 | 49 | 10 | 31 | 20 |
| B | 0.1 | 49 | 10 | 31 | 18 |
| C | 0.1 | 49 | 10 | 33 | 21 |
| — | — | 49 | 10 | 0 | — |
| A | 0.1 | 50 | 10 | 36 | 20 |
| B | 0.1 | 50 | 10 | 33 | 18 |
| C | 0.1 | 50 | 10 | 35 | 21 |
| — | — | 50 | 10 | 0 | — |

TABLE 8

| Drug I | | Drug II | | Growth inhibition rate (%) | Expected value (%) |
|---|---|---|---|---|---|
| Type | Concentration (ppm) | Type | Concentration (ppm) | | |
| A | 0.1 | 51 | 10 | 25 | 20 |
| B | 0.1 | 51 | 10 | 25 | 18 |
| C | 0.1 | 51 | 10 | 30 | 21 |
| — | — | 51 | 10 | 0 | — |
| A | 0.1 | 52 | 10 | 32 | 23 |
| B | 0.1 | 52 | 10 | 30 | 22 |
| C | 0.1 | 52 | 10 | 33 | 24 |
| — | — | 52 | 10 | 4 | — |
| A | 0.1 | 53 | 10 | 40 | 29 |
| B | 0.1 | 53 | 10 | 39 | 28 |
| C | 0.1 | 53 | 10 | 43 | 30 |
| — | — | 53 | 10 | 12 | — |
| A | 0.1 | 54 | 10 | 29 | 22 |
| B | 0.1 | 54 | 10 | 27 | 20 |
| C | 0.1 | 54 | 10 | 33 | 22 |
| — | — | 54 | 10 | 2 | — |
| A | 0.1 | 55 | 10 | 32 | 22 |
| B | 0.1 | 55 | 10 | 30 | 20 |
| C | 0.1 | 55 | 10 | 33 | 23 |
| — | — | 55 | 10 | 3 | — |
| A | 0.1 | 56 | 10 | 74 | 42 |
| B | 0.1 | 56 | 10 | 68 | 41 |
| C | 0.1 | 56 | 10 | 73 | 43 |
| — | — | 56 | 10 | 28 | — |
| A | 0.1 | 57 | 10 | 47 | 20 |
| B | 0.1 | 57 | 10 | 39 | 18 |
| C | 0.1 | 57 | 10 | 47 | 21 |

TABLE 8-continued

| Drug I | | Drug II | | Growth inhibition rate | Expected value |
|---|---|---|---|---|---|
| Type | Concentration (ppm) | Type | Concentration (ppm) | (%) | (%) |
| — | — | 57 | 10 | 0 | — |
| A | 0.1 | — | — | 20 | — |
| B | 0.1 | — | — | 18 | — |
| C | 0.1 | — | — | 21 | — |

From these results, it can be seen that values of the growth inhibition rates measured when using the fungicidal composition according to the present invention are greater than the expected values of the growth inhibition rates calculated according to the above Colby's equation, and all the compositions exhibit a synergistic sterilization effect.

(Control Test for Cucumber Gray Mold Disease)

The drug I and the drug II were dissolved in an organic solvent and a surfactant, and the prepared mixed emulsifiable concentrate was diluted with water to a predetermined concentration, and sprayed to cucumber seedlings that had been cultivated in unglazed pots (cultivar "Sagamihanjiro" cotyledon stage). Additionally, in Tables, the symbol A indicating the drug I represents a nitrogen-containing heterocyclic compound represented by the formula (A), the symbol B indicating the drug I represents a nitrogen-containing heterocyclic compound represented by the formula (B), and the symbol C indicating the drug I represents a nitrogen-containing heterocyclic compound represented by the formula (C). Further, the number indicating the drug II represents each of the compounds described in the numbers described above. Additionally, "-" in Tables represents that the drug was not used.

After air-drying at room temperature, a suspension of the conidia of cucumber gray mold disease pathogens (*Botrytis cinerea*) was inoculated by dropwise addition and held in a dark room at 20° C. with a high humidity for 3, 4, or 5 days. By investigation on the state of lesion appearance in leaves with comparison with a non-treatment case, the controlling effect was determined. The test was carried out in duplicate. In addition, the expected value of the controlling effect was calculated based on Colby's equation.

At the same time, in Comparative Example, in the case of using the drug I only and the case of using the drug II only, the test was carried out by the same method.

The results thereof are shown in Tables 9 to 14.

Additionally, the Colby's equation is $E=M+N-MN/100$. Here, E is the expected value of the controlling effect (%), M is the controlling effect (%) calculated from the measurement with the use of the drug I alone, and N is the controlling effect (%) calculated from the measurement with the use of the drug II alone. Additionally, in Tables, the expected values with the use of the drug alone were the same as the values calculated from the measurement, and were thus not shown.

TABLE 9

(4 days after inoculation)

| Drug I | | Drug II | | | Expected |
|---|---|---|---|---|---|
| Type | Concentration (ppm) | Type | Concentration (ppm) | Control effect (%) | value (%) |
| B | 10 | 2 | 400 | 84 | 82 |
| — | — | 2 | 400 | 64 | — |
| B | 10 | 3 | 1.6 | 80 | 52 |
| — | — | 3 | 1.6 | 3 | — |
| B | 10 | 38 | 100 | 56 | 50 |
| C | 10 | 38 | 100 | 58 | 51 |
| — | — | 38 | 100 | 0 | — |
| B | 10 | — | — | 50 | — |
| C | 10 | — | — | 51 | — |

TABLE 10

(5 days after inoculation)

| Drug I | | Drug II | | | Expected |
|---|---|---|---|---|---|
| Type | Concentration (ppm) | Type | Concentration (ppm) | Control effect (%) | value (%) |
| A | 10 | 1 | 25 | 67 | 43 |
| B | 10 | 1 | 25 | 51 | 44 |
| C | 10 | 1 | 25 | 57 | 47 |
| — | — | 1 | 25 | 0 | — |
| A | 10 | 2 | 100 | 66 | 61 |
| — | — | 2 | 100 | 33 | — |
| A | 10 | 3 | 6.3 | 100 | 94 |

TABLE 10-continued (5 days after inoculation)

| Drug I | | Drug II | | | Expected |
|---|---|---|---|---|---|
| Type | Concentration (ppm) | Type | Concentration (ppm) | Control effect (%) | value (%) |
| C | 10 | 3 | 6.3 | 100 | 94 |
| — | — | 3 | 6.3 | 89 | — |
| A | 10 | 4 | 1.6 | 58 | 43 |
| B | 10 | 4 | 6.3 | 73 | 67 |
| C | 10 | 4 | 1.6 | 100 | 47 |
| — | — | 4 | 1.6 | 0 | — |
| — | — | 4 | 6.3 | 41 | — |
| A | 10 | 5 | 0.4 | 54 | 43 |
| B | 10 | 5 | 1.6 | 50 | 44 |
| C | 10 | 5 | 1.6 | 61 | 47 |
| — | — | 5 | 0.4 | 0 | — |
| — | — | 5 | 1.6 | 0 | — |
| A | 10 | 38 | 400 | 48 | 43 |
| — | — | 38 | — | 0 | — |
| A | 10 | — | — | 43 | — |
| B | 10 | — | — | 44 | — |
| C | 10 | — | — | 47 | — |

TABLE 11

(4 days after inoculation)

| Drug I | | Drug II | | | Expected |
|---|---|---|---|---|---|
| Type | Concentration (ppm) | Type | Concentration (ppm) | Control effect (%) | value (%) |
| B | 10 | 43 | 400 | 83 | 78 |
| — | — | 43 | 400 | 2 | — |
| C | 10 | 44 | 400 | 93 | 81 |
| — | — | 44 | 400 | 22 | — |
| B | 10 | — | — | 78 | — |
| C | 10 | — | — | 76 | — |

TABLE 12

(5 days after inoculation)

| Drug I | | Drug II | | Control effect (%) | Expected value (%) |
|---|---|---|---|---|---|
| Type | Concentration (ppm) | Type | Concentration (ppm) | | |
| A | 10 | 42 | 400 | 91 | 60 |
| C | 10 | 42 | 400 | 86 | 67 |
| — | — | 42 | 400 | 0 | — |
| A | 10 | 43 | 100 | 93 | 60 |
| C | 10 | 43 | 400 | 70 | 67 |
| — | — | 43 | 100 | 0 | — |
| — | — | 43 | 400 | 0 | — |
| A | 10 | 44 | 400 | 88 | 60 |
| B | 10 | 44 | 400 | 82 | 64 |
| — | — | 44 | 400 | 0 | — |
| A | 10 | — | — | 60 | — |
| B | 10 | — | — | 64 | — |
| C | 10 | — | — | 67 | — |

TABLE 13

(4 days after inoculation)

| Drug I | | Drug II | | Control effect (%) | Expected value (%) |
|---|---|---|---|---|---|
| Type | Concentration (ppm) | Type | Concentration (ppm) | | |
| C | 10 | 2 | 100 | 49 | 20 |
| — | — | 2 | 100 | 1 | — |
| A | 10 | 29 | 1.6 | 49 | 37 |
| B | 10 | 29 | 0.4 | 71 | 37 |
| C | 10 | 29 | 6.3 | 100 | 49 |
| — | — | 29 | 0.4 | 0 | — |
| — | — | 29 | 1.6 | 0 | — |
| — | — | 29 | 6.3 | 37 | — |

TABLE 13-continued (4 days after inoculation)

| Drug I | | Drug II | | Control effect (%) | Expected |
|---|---|---|---|---|---|
| Type | Concentration (ppm) | Type | Concentration (ppm) | Type | value (%) |
| B | 10 | 42 | 25 | 44 | 37 |
| — | — | 42 | 25 | 0 | — |
| A | 10 | 58 | 1.6 | 70 | 37 |
| B | 10 | 58 | 6.3 | 81 | 62 |
| C | 10 | 58 | 0.4 | 46 | 19 |
| — | — | 58 | 0.4 | 0 | — |
| — | — | 58 | 1.6 | 0 | — |
| — | — | 58 | 6.3 | 39 | — |
| A | 10 | 59 | 400 | 43 | 37 |
| B | 10 | 59 | 400 | 40 | 37 |
| C | 10 | 59 | 400 | 58 | 19 |
| — | — | 59 | 400 | 0 | — |
| A | 10 | — | — | 37 | — |
| B | 10 | — | — | 37 | — |
| C | 10 | — | — | 19 | — |

TABLE 14

(3 days after inoculation)

| Drug I | | Drug II | | Control effect (%) | Expected |
|---|---|---|---|---|---|
| Type | Concentration (ppm) | Type | Concentration (ppm) | Type | value (%) |
| A | 10 | 60 | 25 | 63 | 52 |
| B | 10 | 60 | 25 | 63 | 54 |
| C | 10 | 60 | 25 | 60 | 54 |
| — | — | 60 | 25 | 0 | — |
| A | 10 | 61 | 6.3 | 62 | 52 |
| B | 10 | 61 | 6.3 | 58 | 54 |
| C | 10 | 61 | 100 | 79 | 54 |
| — | — | 61 | 6.3 | 0 | — |
| — | — | 61 | 100 | 0 | — |
| A | 10 | — | — | 52 | — |
| B | 10 | — | — | 54 | — |
| C | 10 | — | — | 54 | — |

(Control Test for Cucumber Powdery Mildew Disease)

The drug I and the drug II were dissolved in an organic solvent and a surfactant, and the prepared mixed emulsifiable concentrate was diluted with water to a predetermined concentration, and sprayed to cucumber seedlings that had been cultivated in unglazed pots (cultivar "Sagamihanjiro", cotyledon stage). Additionally, in Tables, the symbol A indicating the drug I represents a nitrogen-containing heterocyclic compound represented by the formula (A), the symbol B indicating the drug I represents a nitrogen-containing heterocyclic compound represented by the formula (B), and the symbol C indicating the drug I represents a nitrogen-containing heterocyclic compound represented by the formula (C). Further, in Tables, the number indicating the drug II represents each of the compounds described in the numbers described above. Additionally, "-" in Tables represents that the drug was not used.

After air-drying at room temperature, the conidia of cucumber powdery mildew disease pathogens (*Sphaerotheca fuliginea*) was inoculated by shaking off and held in a warm room for 7 days. By investigation on the state of lesion appearance in leaves with comparison with a non-treatment case, the controlling effect was determined. The test was carried out in duplicate. In addition, the expected value of the controlling effect was calculated based on Colby's equation.

At the same time, in Comparative Example, in the case of using the drug I only and the case of using the drug II only, the test was carried out by the same method.

The results thereof are shown in Table 15.

Additionally, the Colby's equation is $E=M+N-MN/100$. Here, E is the expected value of the controlling effect (%), M is the controlling effect (%) calculated from the measurement with the use of the drug I alone, and N is the controlling effect (%) calculated from the measurement with the use of the drug II alone. Additionally, in Tables, the expected values with the use of the drug alone were the same as the values calculated from the measurement, and were thus not shown.

TABLE 15

| Drug I | | Drug II | | Control effect (%) | Expected |
|---|---|---|---|---|---|
| Type | Concentration (ppm) | Type | Concentration (ppm) | Type | value (%) |
| A | 10 | 60 | 6.3 | 80 | 46 |
| B | 10 | 60 | 25 | 100 | 80 |
| C | 10 | 60 | 25 | 100 | 65 |
| — | — | 60 | 6.3 | 10 | — |
| — | — | 60 | 25 | 50 | — |
| A | 10 | 61 | 6.3 | 60 | 40 |
| C | 10 | 61 | 6.3 | 100 | 30 |
| — | — | 61 | 6.3 | 0 | — |
| A | 10 | — | — | 40 | — |
| B | 10 | — | — | 60 | — |
| C | 10 | — | — | 30 | — |

From these results, it can be seen that the value of the controlling effect measured in the case of using the fungicidal compositions according to the present invention exceeded the expected value of the controlling effect calculated according to the above Colby's equation, and all the compositions exhibit a synergistic sterilization effect.

INDUSTRIAL APPLICABILITY

The agricultural and horticultural fungicidal composition of the present invention exhibits an excellent controlling effect on plant diseases even at very low doses and does not pose a concern for harmful effects on useful plants. Therefore, the present invention can be suitably used in agricultural and horticultural fungicidal compositions, and thus, the present invention is extremely useful industrially.

The invention claimed is:

1. An agricultural and horticultural fungicidal composition comprising:
   at least one compound I of a nitrogen-containing heterocyclic compound represented by the following formula (C), and salts thereof:

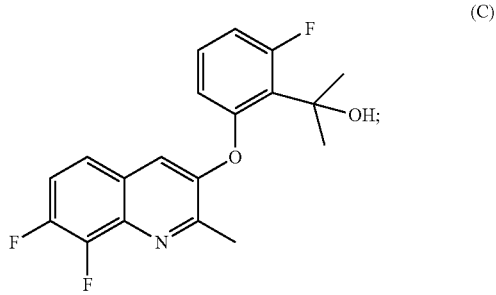 [SMILES: Cc1nc2c(F)c(F)ccc2cc1Oc1cccc(F)c1C(C)(C)O]

(C)

and
   at least one compound II having a fungicidal activity that is selected from the group consisting of an SBI agent, an acid amide-based fungicide, an organic (thio)phosphate-based agent, a guanidine-based fungicide, a mitochondrial electron transport chain complex III inhibitor, an SH inhibitor, cyflufenamid, proquinazid, quinoxyfen, a compound represented by the following formula (9), and salts thereof:

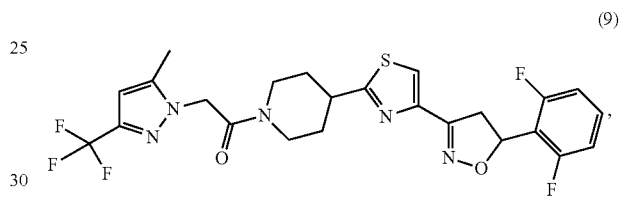

(9)

wherein
the SBI agent is at least one compound selected from the group consisting of difenoconazole, and prothioconazole;
the acid amide-based fungicide is at least one compound selected from the group consisting of zoxamide, flutolanil, carboxin, and thifluzamide;
the organic (thio)phosphate-based agent is tolclofos-methyl;
the guanidine-based fungicide is iminoctadine;
the mitochondrial electron transport chain complex III inhibitor is at least one compound selected from the group consisting of a QoI agent, a QiI agent, and ametoctradin;
the QoI agent is at least one compound selected from the group consisting of trifloxystrobin, kresoxim-methyl, and pyribencarb;
the QiI agent is cyazofamid; and
the SH inhibitor is at least one compound selected from the group consisting of manzeb, maneb, and chlorothalonil;
in a weight ratio of said compound I:said compound II selected from ranges of from 5:1 to 1:100,
wherein the composition has a synergistic fungicidal effect of said compound I and said compound II.

* * * * *